(12) United States Patent
Ulrich et al.

(10) Patent No.: US 7,022,721 B1
(45) Date of Patent: Apr. 4, 2006

(54) METHOD AND COMPOSITION FOR REJUVENATING CELLS, TISSUES, ORGANS, HAIR AND NAILS

(76) Inventors: Peter C Ulrich, 8921 NW. Bartholomew Dr., Portland, OR (US) 97229; Sheng Ding Fang, 28 BArker St., Apt. D2, Mount Kisco, NY (US) 10549; Michael L Brines, 1 Wepawang Rd., Woodbridge, CT (US) 06525; Qiao-Wen Xie, 30 Sidehill La., Yonkers, NY (US) 10710; Anthony Cerami, 121 Farrington Ave., Sleepy Hollow, NY (US) 10591

( * ) Notice: Subject to any disclaimer, the term of this patent is extended or adjusted under 35 U.S.C. 154(b) by 30 days.

(21) Appl. No.: 10/794,024

(22) Filed: Mar. 8, 2004

Related U.S. Application Data

(62) Division of application No. 10/072,712, filed on Feb. 7, 2002, now Pat. No. 6,777,557.

(60) Provisional application No. 60/267,226, filed on Feb. 7, 2001.

(51) Int. Cl.
*A61K 31/428* (2006.01)
*C07D 277/84* (2006.01)

(52) U.S. Cl. ................ 514/366; 548/366; 548/150
(58) Field of Classification Search .......... 514/366; 548/366, 150
See application file for complete search history.

(56) References Cited

U.S. PATENT DOCUMENTS

| | | | |
|---|---|---|---|
| 6,319,934 B1 * | 11/2001 | Wagle et al. | 514/365 |
| 6,777,557 B1 * | 8/2004 | Ulrich et al. | 548/150 |
| 6,790,859 B1 * | 9/2004 | Wagle et al. | 514/365 |

FOREIGN PATENT DOCUMENTS

JP 09-241614 * 9/1997

OTHER PUBLICATIONS

Brindley et al., "Routes to pyrrolo[2,1-b] thiazole-5-carbaldehydes . . . ", (abstract only), Journal of the chemical society, Perkin Transactions 1: Organic and Bio-Organic Chemistry, 1986, vol. (7), pp. 1255-1259.*

* cited by examiner

*Primary Examiner*—Vickie Kim
(74) *Attorney, Agent, or Firm*—Frederick Hamble

(57) ABSTRACT

In one embodiment, the present invention relates to compounds and compositions including pharmaceutical compositions containing the compounds and associated methods that uncouple sugar-mediated coupling of proteins, lipids, nucleic acids, and other biomaterials, and any combination thereof. In another embodiment, the compositions and associated methods have utility in vivo to reduce the deleterious effects of sugar-mediated coupling processes in an organism, when the organism is exposed to the compound or composition internally, by ingestion, transdermal application, or other means. In yet another embodiment, the compositions and associated methods are useful for the ex-vivo treatment of organs, cells and tissues and external treatment of hair, nails and skin to rejuvenate them by changing deformability and increase the tissue diffusion coefficient. In a further embodiment, the present invention relates to novel compounds and pharmaceutical compositions.

1 Claim, 2 Drawing Sheets

METHOD AND COMPOSITION FOR REJUVENATING CELLS, TISSUES, ORGANS, HAIR AND NAILS

CROSS-REFERENCE TO RELATED APPLICATIONS

This application is a divisional of U.S. patent application Ser. No. 10/072,712, filed Feb. 7, 2002, now U.S. Pat. No. 6,777,557, which claims priority to U.S. Provisional Application Ser. No. 60/267,226, filed Feb. 7, 2001, the entireties of which are incorporated herein by reference.

BACKGROUND OF THE INVENTION

The present invention relates generally to the uncoupling of sugar-mediated coupling of proteins, lipids, nucleic acids, and other biomaterials, and any combination thereof, resulting from their reaction with glucose and other reducing sugars. The reaction between glucose and protein amino groups was studied in detail by Maillard in 1912, who observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and the polypeptide chain, and that the proteins are resultantly cross-linked and correspondingly exhibit decreased bioavailability. U.S. Pat. No. 6,007,865 discloses that these reactions occur in vivo at normal glucose levels. U.S. Pat. No. 6,007,865 further terms these reactions as advanced glycosylation (or glycation) end products (AGEs).

Several therapeutic approaches have been attempted based upon intervening in the accumulation of AGEs in vivo. One approach, exemplified in U.S. Pat. No. 4,758,583, concerns the inhibition of the formation of AGEs from their precursors, by the administration of agents such as aminoguanidine and related compounds. By reacting with an early glycosylation product that results from the original reaction between the target protein and glucose, this patent discloses that these agents block the formation of AGEs and further formation of AGEs and cross-links in tissues is inhibited.

U.S. Pat. Nos. 5,656,261, 5,853,703, 6,007,865, and 6,121,300, and in P.C.T. Intl. Appl. WO97/42175, disclose agents and methods that reverse (also termed cleave or break) existing AGE cross-links in vitro and in vivo. Specifically, these patents disclose a mechanism of protein crosslinking by sugars, involving formation of a 6-hydroxy-2,3-hexanedione protein—protein cross-linking structure which has an epsilon amino group of one protein attached to the 1 position, and a nucleophilic side chain of another protein attached to the 5 position. Further, these patents disclosed compounds such as 4,5-dimethyl-3-(2-oxo-2-phenylethyl)thiazolium bromide, which were claimed to have broken protein—protein cross-links in a manner consistent with a mechanism involving transient formation of a carbanion by deprotonation of the unsubstituted 2-position of the thiazolium ring, followed by attack of the carbanion at one of the ketone carbonyls of the hypothetical 6-hydroxy-2,3-hexanedione protein—protein cross-linking structure. Subsequent rearrangements known for such thiazolium adducts could lead to cleavage of the bond between the carbonyl carbons, resulting in formation of an aldehyde fragment and a carboxylic acid fragment.

SUMMARY OF THE INVENTION

In one embodiment of the present invention, compositions and methods are disclosed for uncoupling of sugar-mediated coupling of proteins, lipids, nucleic acids, and other biomaterials, and any combination thereof. In another embodiment, sugar-mediated coupling caused by other reactive sugars present in vivo or in foodstuffs, including ribose, galactose and fructose may also be uncoupled by the methods and compositions of the present invention. The compositions and methods comprise the below disclosed compounds.

In another embodiment, the compositions have utility in vivo to reduce the deleterious effects of sugar-mediated coupling processes in an organism, when the organism is exposed to the compound or composition internally, by ingestion, transdermal application, or other means. The compositions comprise the below disclosed compounds.

In yet another embodiment, the compositions are useful for the ex-vivo treatment of organs, cells and tissues and external treatment of hair, nails and skin to rejuvenate them by changing deformability and increase the tissue diffusion coefficient. This treatment is accomplished by bathing or perfusing the biological material outside of the body. The compositions comprise the below disclosed compounds.

In still another embodiment, the compositions have utility in treatment of proteinaceous organism-derived materials of commerce comprising fur, leather, feathers, down, silk, wool, gut, or the like, to enhance their softness and suppleness of texture and reduce their stiffness and brittleness, thus increasing the value and functionality of such materials. Such treatment is accomplished by exposing the organism-derived material to the composition or a solution of the composition in water or other suitable vehicle.

In a further embodiment, the present invention relates to the above-identified compositions that comprises one or more compounds of thiazole derivatives where carbon substituents are attached to the 2 position of the thiazolium nucleus and represented by formula (I):

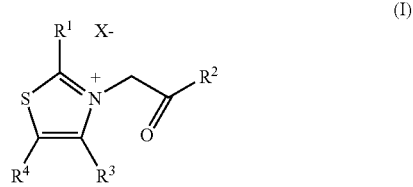

wherein $R^1$ is a $C_1-C_{18}$ alkyl group, or the group —CH($R^5$—OH or the group —CH($R^5$—OC(=O)—$R^6$ wherein $R_5$ is a $C_{1-18}$ alkyl group and $R_6$ is selected from the group consisting of $C_{1-18}$ alkyl, phenyl, halosubstituted phenyl, $C_1-C_{18}$ alkoxysubstituted phenyl and naphthyl;

$R_2$ is selected from the group consisting of hydroxy, phenyl, halosubstituted phenyl, $C_1-C_{18}$ alkoxysubstituted phenyl, a $C_{5-7}$ aromatic, unsaturated or saturated heterocyclic ring having one to three heteroatoms selected from the group consisting of N, O and S;

$R_3$ and $R_4$ are independently selected from the group consisting of hydrogen, $C_1-C_{18}$ alkyl or hydroxyalkyl, or phenyl, or $R_3$ and $R_4$ together are a bridge of 3–6 methylene units, or $R_3$ and $R_4$ together with their ring atoms may be an aromatic ring system of 6–10 carbons, optionally substituted with one or more halo, lower alkyl, lower alkoxy, or amino groups; and $X^-$ is halide, preferably chloride or bromide, or other pharmaceutically acceptable anion.

Certain compounds of formula (I) may undergo cycloelimination to form lactones or cyclic enol ethers constituting novel thiazolooxazinium derivatives which are also embodiments of this invention.

In a further embodiment the present invention relates to novel compounds of formula:

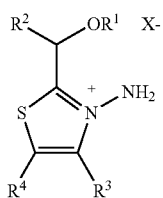

wherein $R^1$ is hydrogen, or —C(=O)—$R^6$ wherein $R^6$ is selected from the group consisting of $C_1$–$C_8$ alkyl, $C_1$–$C_{18}$ alkoxy, phenyl, halosubstituted phenyl, $C_1$–$C_{18}$ alkoxysubstituted phenyl and naphthyl;

$R^2$ is hydrogen, phenyl or a $C_{1-5}$ alkyl group;

$R^3$ and $R^4$ are independently selected from the group consisting of hydrogen, $C_1$–$C_{18}$ alkyl or hydroxyalkyl, or phenyl, or $R^3$ and $R^4$ together are a bridge of 3–6 methylene units, or $R^3$ and $R^4$ together with their ring atoms may be an aromatic ring system of 6–10 carbons, optionally substituted with one or more halo, lower alkyl, lower alkoxy, or amino groups; and $X^-$ is mesitylene-2-sulfonate or other pharmaceutically acceptable anion.

In another embodiment the present invention relates to the above-identified compositions that comprise one or more compounds of naphthothiazole derivatives of formula (II):

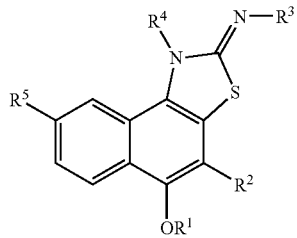

wherein $R^1$ is selected from the group consisting of H, $C_{1-5}$ lower alkyl, $C_{1-18}$ lower alkanoyl, and aroyl;

$R^2$ is selected from the group consisting of hydrogen and $C_{1-5}$ lower alkyl;

$R^3$ is selected from the group consisting of lower alkyl, $C_3$–$C_8$ cycloalkyl, phenyl, 1[(aminoiminomethyl)hydrazono]ethyl substituted phenyl, naphthyl, or aminoalkyl of structure:

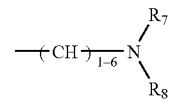

wherein $R^7$ and $R^8$ are independently selected from the group consisting of hydrogen, $C_1$–$C_6$ alkyl, $C_1$–$C_6$ hydroxyalkyl, or $R^7$ and $R^8$ taken together with the nitrogen atom form a $C_4$–$C_7$ heterocyclic ring optionally containing one or two additional heteroatoms selected from the group consisting of N, O or sulfur;

$R^4$ is selected from the group consisting of methyl, lower alkyl, or aminoalkyl of structure

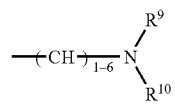

wherein $R^9$ and $R^{10}$ are independently selected from the group consisting of hydrogen, $C_1$–$C_6$ alkyl, $C_1$–$C_6$ hydroxyalkyl, or $R^9$ and $R^{10}$ taken together with the nitrogen atom form a $C_4$–$C_7$ heterocyclic ring optionally containing one or two additional heteroatoms selected from the group consisting of N, O or sulfur; and $R^5$ is selected from the group consisting of hydrogen, acetyl and 1-[(aminoiminomethyl)hydrazono]ethyl;

or hydrochloride salts thereof, or other pharmaceutically acceptable salts thereof.

In a further embodiment, the present invention relates to the above-identified compositions that comprises one or more compounds of pyridinium and pyrimidinium derivatives of formula (III):

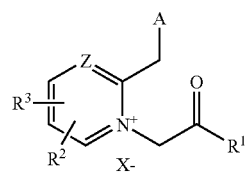

(III)

wherein A is hydrogen, cyano, or a $C_6$–$C_{10}$ aryl group, said aryl groups optionally substituted by one or more lower alkyl, lower alkoxy, or halo groups;

Z is CH or N;

$R^1$ is hydroxy, $C_1$–$C_{18}$ alkoxy, amino optionally substituted with 1–2 independent $C_1$–$C_{18}$ alkyl groups, phenyl, halosubstituted phenyl, $C_1$–$C_{18}$ alkoxysubstituted phenyl, or a $C_{4-7}$ aromatic or unsaturated or saturated heterocyclic ring having one to three heteroatoms selected from the group consisting of N, O, or S, with the proviso that at least one heteroatom is nitrogen and said nitrogen is directly bonded to the carbonyl group; and $R^2$ and $R^3$ are independently selected from hydrogen, amino, or $C_1$–$C_{18}$ alkyl groups, or $R^2$ and $R^3$ taken together may form a carbocyclic or heterocyclic ring, and X⁻ is halide, preferably chloride or bromide, or other pharmaceutically acceptable anion.

In another embodiment, the present invention relates to the above-identified compositions that comprises one or more compounds of 1-aminopyrimidinium derivatives of formula (IV):

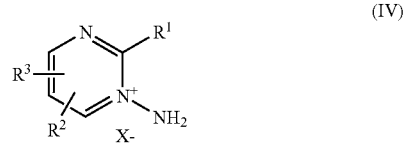

(IV)

wherein R¹ is selected from:
  amino,
  methyl,
  cyanomethyl,
  the group —CH₂—A where A is a C₆–C₁₀ aryl group optionally substituted by one or more lower alkyl, lower alkoxy or halo groups, or
  the group —CH₂—C(=O)—Z where Z is selected from hydroxy, C₁–C₁₈ alkoxy, amino optionally substituted with 1–2 C₁–C₁₈ alkyl groups, a C₆–C₁₀ aryl group optionally substituted by one or more lower alkyl or halo groups, or a C₄₋₇ aromatic or unsaturated or saturated heterocyclyl group having one to three heteroatoms selected from the group consisting of N, O, or S;
R² and R³ are independently selected from hydrogen, amino, lower alkoxy, or C₁–C₈ alkyl groups, or if R² and R³ are on adjacent atoms then R² and R³ taken together with their ring atoms may form a fused carbocyclic or heterocyclic ring; and
X⁻ is mesitylene-2-sulfonate or other pharmaceutically acceptable anion.

In yet another embodiment, the present invention relates to the above-identified compositions that comprises one or more compounds of imidazolium derivatives of formula (V):

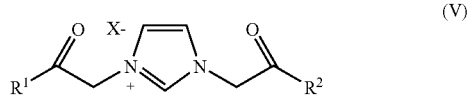

(V)

wherein R¹ and R² are independently selected from hydroxy, lower alkoxy, amino optionally substituted with 1–2 lower alkyl groups, aryl, halosubstituted aryl, (lower alkyl)substituted aryl, or a C₅₋₇ unsaturated or saturated heterocyclic ring having one to three heteroatoms selected from the group consisting of N, O, and S and X⁻ is halide, preferably chloride or bromide, or other pharmaceutically acceptable anion.

The ability of the compositions of the present invention to uncouple sugar-mediated coupling of proteins, lipids, nucleic acids, and other biomaterials, and any combination thereof carries with it significant implications in all applications where sugar-mediated coupling is a serious detriment. In the area of food technology, for instance, the uncoupling of sugar-mediated coupling would confer a reduction of the increased toughness resulting from the formation of sugar-mediated coupling during storage. In yet another embodiment, the application of the composition of the present invention has particular benefit in vivo as sugar-mediated coupling may adversely affect several of the significant protein masses or other biomaterials of the body, among them collagen, elastin, lens proteins, the kidney glomerular basement membrane, nucleic acids and lipids. These proteins or other biomaterials deteriorate both with age (hence the application of the term "protein aging") and more rapidly as a consequence of diabetes. Accordingly, the ability to uncouple sugar mediated coupling of proteins, lipids, nucleic acids, and other biomaterials, and any combination thereof in the body provides for treatment of the complications of diabetes and aging for instance, or ex-vivo treatment of transplantable organs as another instance, or external treatment of hair, skin and nails as yet another instance, and thereby improving the quality and, perhaps, duration of animal and human life.

DETAILED DESCRIPTION OF THE INVENTION

Figure 1:
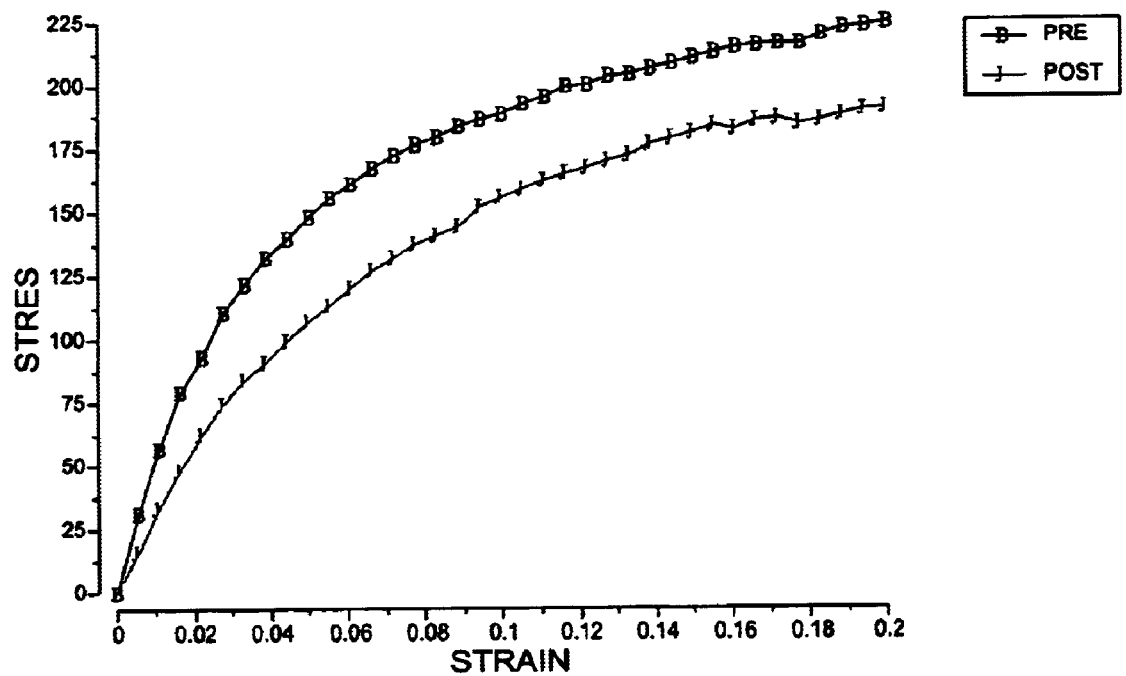
FIG. 1 shows that a composition of the present invention, FP-053, decreases the stiffness of hair after treatment.

It has now been discovered that the theory of crosslinking structures and of reversing the already formed advanced glycosylation end products, which are disclosed in U.S. Pat. Nos. 5,656,261, 5,853,703, 6,007,865, and 6,121,300, and in P.C.T. Intl. Appi. WO97/42175 may be questionable. The reason for the current questioning is based on at least the following discoveries. First, it is believed that the Amadori dione crosslink has never been isolated. Second, it is believed that attempts to make the Amadori dione crosslink have been unsuccessful. Third, it has now been discovered that novel compounds having carbon substituents attached to the 2 position of the thiazolium nucleus, and having different structures from the previously described compounds act as "breakers" for advanced glycosation endproducts ("AGE") cross-linking but, based on the previous disclosures, would not have been anticipated to be structurally capable of acting as "breakers." This also places in question both the existence of the Amadori dione crosslinking structure itself, and the hypothesis that its chemical cleavage is the mechanism of action of AGE "breakers" of the prior art such as 4,5-dimethyl-3-(2-oxo-2-phenyl)ethylthiazolium bromide.

In one embodiment of the present invention, compounds and compositions including pharmaceutical compositions containing the compounds detailed below and associated methods are described that uncouple sugar-mediated coupling of proteins, lipids, nucleic acids, and other biomaterials, and any combination thereof.

It is believed that the sugar-mediated coupling of proteins, lipids, nucleic acids, and other biomaterials, and any combination thereof can have at least three effects on an animal. These three effects are biophysical, immunological and biochemical. With respect to the biophysical effect, the response can be measured by, for example, biomechanical and/or diffusional parameters. With respect to the immunological effect, the response can be measured by, for example, inflammatory fibrosis. Finally, with respect to the biochemical effect, the response can be measured by, for example, altered tissue remodeling and/or macromolecular trapping. Since the composition of the present invention uncouples the sugar-mediated coupling of the biomaterials, the composition may be used to reduce the deleterious effects caused by the sugar-mediated coupling and thus, improve the biophysical, immunological and/or biochemical effects on an animal.

In one specific embodiment, the composition of the present invention comprises one or more compounds of thiazole derivatives where a carbon substituent is attached to the 2 position of the thiazolium nucleus as represented by formula (I):

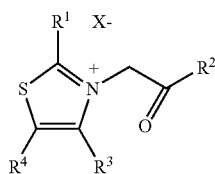

(I)

wherein $R^1$ is a $C_1$–$C_{18}$ alkyl group, or the group —CH($R^5$)OH, or the group —CH($R^5$)—OC(=O)$R^6$ wherein $R_5$ is a $C_{1-18}$ alkyl group and $R_6$ is selected from the group consisting of $C_1$–$C_{18}$ alkyl, phenyl, halosubstituted phenyl, $C_1$–$C_{18}$ alkoxysubstituted phenyl and naphthyl;

$R_2$ is selected from the group consisting of hydroxy, phenyl, halosubstituted phenyl, $C_1$–$C_{18}$ alkoxysubstituted phenyl, a $C_{5-7}$ aromatic, unsaturated or saturated heterocyclic ring having one to three heteroatoms selected from the group consisting of N, O and S;

$R_3$ and $R_4$ are independently selected from the group consisting of hydrogen, $C_1$–$C_{18}$ alkyl or hydroxyalkyl, or phenyl, or $R_3$ and $R_4$ together are a bridge of 3–6 methylene units, or $R_3$ and $R_4$ together with their ring atoms may be an aromatic ring system of 6–10 carbons, optionally substituted with one or more halo, lower alkyl, lower alkoxy, or amino groups; and $X^-$ is halide, prefer ably chloride or bromide, or other pharmaceutically acceptable anion.

Representative compounds of the above embodiment known to the prior art include:
2-methyl-3-(2-oxopropyl)thiazolium bromide
2-methyl-3-(2-oxo-2-phenylethyl)thiazolium bromide Certain compounds of the above embodiment are novel, comprising those having the structure

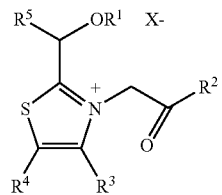

wherein
$R^1$ is hydrogen, or —C(=O)$R^6$ wherein $R^6$ is selected from the group consisting of $C_1$–$C_{18}$)$_8$ alkyl, $C_1$–$C_8$ alkoxy, phenyl, halosubstituted phenyl, $C_{1-18}$ alkoxysubstituted phenyl and naphthyl;

$R^2$ is selected from the group consisting of hydroxy, $C_1$–$C_{18}$ is alkoxy, amino optionally substituted with 1–2 independent $C_1$–$C_8$ alkyl groups, phenyl, halosubstituted phenyl, $C_1$–$C_{18}$ alkoxysubstituted phenyl, naphthyl, or a 4 to 10 membered aromatic heterocyclic or unsaturated heterocyclic or saturated heterocyclic ring system of 1 to 2 rings having one to three heteroatoms selected from the group consisting of N, O and S;

$R^3$ and $R^4$ are independently selected from the group consisting of hydrogen, $C_1$–$C_{18}$ alkyl or hydroxyalkyl, or phenyl, or $R^3$ and $R^4$ together are a bridge of 3–6 methylene units, or $R^3$ and $R^4$ together with their ring atoms may be an aromatic ring system of 6–10 carbons, optionally substituted with one or more halo, lower alkyl, lower alkoxy, or amino groups;

$R^5$ is hydrogen, phenyl or a $C_{1-5}$ alkyl group; and
$X^-$ is a pharmaceutically acceptable anion such as halide, preferably chloride or bromide.

Representative novel compounds of the above embodiment include, but are not limited to:
3-(2-Oxo-2-phenylethyl)-2-(1-hydroxyethyl)thiazolium bromide;
3-(2-Oxo-2-phenylethyl)-2-(1-benzoyloxyethyl)thiazolium bromide;
2-(1-hydroxyethyl)-3-[2-(1-pyrrolidinyl)-2-oxoethyl]thiazolium chloride;
2,4-Dimethyl-3-(2-oxo-2-phenylethyl)thiazolium bromide;
2-Ethyl-4-methyl-3-(2-oxo-2-phenylethyl)thiazolium bromide;
3-carboxymethyl-2-(1-hydroxyethyl)thiazolium bromide;
1-(2-methoxy-2-oxoethyl)-2-(1-hydroxyethyl)thiazolium bromide
3-[2-Oxo-2-phenylethyl]-2-(1-acetoxyethyl)thiazolium bromide;
3-[2-Oxo-2-(1-pyrrolidinyl)ethyl]-2-(1-acetoxyethyl)thiazolium bromide; and
4,5-dimethyl-2-(1-hydroxyethyl)-3-(2-oxo-2-phenylethyl) thiazolium bromide.

The compounds of formula (I) differ materially from thiazolium AGE breakers disclosed in U.S. Pat. Nos. 5,656,261, 5,853,703, 6,007,865, and 6,121,300, in that the thiazolium derivatives of formula I of the present invention have an alkyl or substituted alkyl group attached to position 2 of the thiazole ring. The utility of such compounds as AGE breakers is inconsistent with the mechanistic discussion presented in U.S. Pat. Nos. 5,656,261, 5,853,703, 6,007,865, and 6,121,300.

Certain compounds of formula (I) may undergo cycloelimination to form novel thiazolooxazinium derivatives which are also embodiments of this invention. These include lactones and cyclic enol ethers. A class of novel lactone thiazolooxazinium compounds which are an embodiment of the present invention have the structure

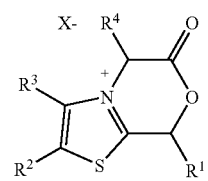

wherein
$R^1$ and $R^4$ are independently selected from hydrogen, phenyl or $C_1$–$C_5$ alkyl;
$R^2$ and $R^3$ are independently selected from the group consisting of hydrogen, $C_1$–$C_{18}$ alkyl or hydroxyalkyl, or phenyl, or $R^2$ and $R^3$ together are a bridge of 3–6 methylene units, or $R^2$ and $R^3$ together with their ring atoms may be an aromatic ring system of 6–10 carbons, optionally substituted with one or more halo, lower alkyl, lower alkoxy, or amino groups; and X⁻ is a pharmaceutically acceptable anion such as halide, preferably chloride or bromide.

Examples of such novel lactone thiazolooxazinium derivatives include, but are not limited to:

5,6-Dihydro-8-methyl-6-oxo-8H-thiazolo[2,3-c](1,4)oxazin-4-ium bromide, mp 214–215.5 C.

5,6-Dihydro-2,3,8-trimethyl-6-oxo-8H-thiazolo[2,3-c](1,4)oxazin-4-ium bromide.

A class of novel cyclic enol ether thiazolooxazinium compounds which are an embodiment of the present invention have the structure

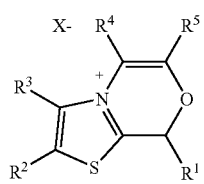

wherein
$R^1$ and $R^4$ are independently selected from hydrogen, phenyl or $C_1$–$C_5$ alkyl;
$R^2$ and $R^3$ are independently selected from the group consisting of hydrogen, $C_1$–$C_{18}$ alkyl or hydroxyalkyl, or phenyl, or $R^2$ and $R^3$ together are a bridge of 3–6 methylene units, or $R^2$ and $R^3$ together with their ring atoms may be an aromatic ring system of 6–10 carbons, optionally substituted with one or more halo, lower alkyl, lower alkoxy, or amino groups;
$R^5$ is phenyl, halosubstituted phenyl, $C_1$–$C_{18}$ alkoxysubstituted phenyl, or a $C_{5-7}$ aromatic or unsaturated or saturated heterocyclic ring having one to three heteroatoms selected from the group consisting of N, O and S; and X⁻ is a pharmaceutically acceptable anion such as halide, preferably chloride or bromide.

Examples of such novel cyclic enol ether thiazolooxazinium derivatives include, but are not limited to:

2,3,8-trimethyl-6-phenyl-8H-thiazolo[2,3-c](1,4)oxazin-4-ium bromide, mp 236 C (dec.);

3,8-dimethyl-6-phenyl-8H-thiazolo[2,3-c](1,4)oxazin-4-ium bromide.

In an additional embodiment, the composition of the present invention comprises novel aminothiazolium compounds of formula:

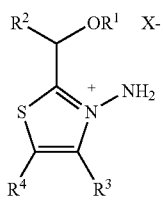

wherein
$R^1$ is hydrogen, or —C(=O)$R^6$ wherein $R^6$ is selected from the group consisting of $C_1$–$C_{18}$ alkyl, $C_1$–$C_{18}$ alkoxy, phenyl, halosubstituted phenyl, $C_1$–$C_{18}$ alkoxysubstituted phenyl and naphthyl;
$R^2$ is hydrogen, phenyl or a $C_{1-5}$ alkyl group;

$R^3$ and $R^4$ are independently selected from the group consisting of hydrogen, $C_1$–$C_{18}$ alkyl or hydroxyalkyl, or phenyl, or $R^3$ and $R^4$ together are a bridge of 3–6 methylene units, or $R^3$ and $R^4$ together with their ring atoms may be an aromatic ring system of 6–10 carbons, optionally substituted with one or more halo, lower alkyl, lower alkoxy, or amino groups; and X⁻ is mesitylene-2-sulfonate or other pharmaceutically acceptable anion.

Representative novel compounds of the above embodiment include, but are not limited to:

3-amino-2-(1-hydroxyethyl)thiazolium mesitylene-2-sulfonate, mp 105–107 C; and 3-amino-4,5-dimethyl-2-(1-hydroxyethyl)thiazolium mesitylene-2-sulfonate.

In another embodiment, the composition of the present invention comprises one or more compounds of naphthothiazole derivatives of formula (II):

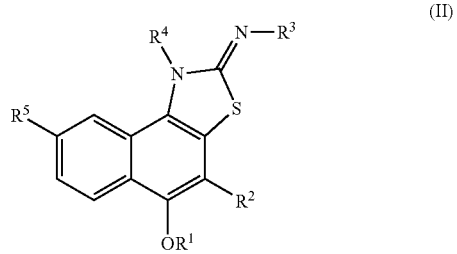

wherein
$R^1$ is selected from the group consisting of H, $C_{1-5}$ lower alkyl, $C_{1-18}$ lower alkanoyl, and aroyl;
$R^2$ is selected from the group consisting of hydrogen and $C_{1-5}$ lower alkyl;
$R^3$ is selected from the group consisting of lower alkyl, $C_3$–$C_8$ cycloalkyl, phenyl, 1-[(aminoiminomethyl)hydrazono]ethyl substituted phenyl, naphthyl, or aminoalkyl of structure:

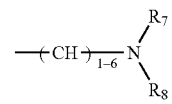

wherein $R^7$ and $R^8$ are independently selected from the group consisting of hydrogen, $C_1$–$C_6$ alkyl, $C_1$–$C_6$ hydroxyalkyl, or $R^7$ and $R^8$ taken together with the nitrogen atom form a $C_4$–$C_7$ heterocyclic ring optionally containing one or two additional heteroatoms selected from the group consisting of N, O or sulfur;

$R^4$ is selected from the group consisting of methyl, lower alkyl, or aminoalkyl of structure

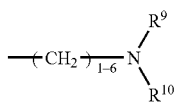

wherein $R^9$ and $R_{10}$ are independently selected from the group consisting of hydrogen, $C_1$–$C_6$ alkyl, $C_1$–$C_6$ hydroxyalkyl, or $R^9$ and $R_{10}$ taken together with the nitrogen atom form a $C_4$–$C_7$ heterocyclic ring optionally containing one or two additional heteroatoms selected from the group consisting of N, O or sulfur; and $R^5$ is selected from the group consisting of hydrogen, acetyl and 1-[(aminoiminomethyl)hydrazono]ethyl;

or hydrochloride salts thereof, or other pharmaceutically acceptable salts thereof.

Representative naphthothiazole compounds of the above embodiment known to the prior art include:

1-ethyl-2-(ethylimino)-1,2-dihydro-4-methylnaphtho[1,2-d]thiazol-5-ol monohydrochloride;
1,2-dihydro-1,4-dimethyl-2-[[3-(4-methyl-1-piperazinyl)propyl]imino]naphtho[1,2-d]thiazol-5-ol trihydrochloride;
2-[[3-[bis(2-hydroxyethyl)amino]propyl]imino]-1,2-dihydro-1,4-dimethylnaphtho[1,2-d]thiazol-5-ol dihydrochloride;
1,2-dihydro-4-methyl-1-(2-propenyl)-2-(2-propenylimino)naphtho[1,2-d]thiazol-5-ol monohydrochloride;
4-methyl-2-(2-propenylamino)naphtho[1,2-d]thiazol-5-ol monohydrochloride;
2-(cyclohexylimino)-5-hydroxy-4-methylnaphtho[1,2-d]thiazole-1 (2H)-ethanol monohydrochloride;
1,2-dihydro-2-[(2-hydroxyethyl)imino]-1,4-dimethylnaphtho[1,2-d]thiazol-5-ol monohydrochloride;
1,2-dihydro-1,4-dimethyl-2-(phenylimino)naphtho[1,2-d]thiazol-5-ol monohydrochloride;
1,2-dihydro-4-methyl-2-(phenylimino)naphtho[1,2-d]thiazol-5-ol monohydrochloride;
1,2-dihydro-1,4-dimethyl-2-(methylimino)naphtho[1,2-d]thiazol-5-ol monohydrochloride;
1-propyl-2-(propylimino)-1,2-dihydro-4-methylnaphtho[1,2-d]thiazol-5-ol monohydrochloride;
1-butyl-2-(butylimino)-1,2-dihydro-4-methylnaphtho[1,2-d]thiazol-5-ol monohydrochloride;
1-hexyl-2-(hexylimino)-1,2-dihydro-4-methylnaphtho[1,2-d]thiazol-5-ol monohydrochloride;
1,2-dihydro-4-methyl-1-(2-methylpropyl)-2-[(2-methylpropyl)imino]naphtho[1,2-d]thiazol-5-ol monohydrochloride;
2-amino-5-hydroxynaphtho[1,2-d]thiazole hydrochloride;
2-amino-5-hydroxy-4-methylnaphtho[1,2-d]thiazole hydrochloride;
5-hydroxy-4-methyl-2-(methylamino)naphtho[1,2-d]thiazole hydrochloride;
2-(ethylamino)-5-hydroxy-4-methylnaphtho[1,2-d]thiazole hydrochloride;
5-hydroxy-2-[(3-methoxyphenyl)amino]-4-methylnaphtho[1,2-d]thiazole hydrochloride;
1,4-dimethyl-5-hydroxy-2-[(2-methoxyethyl)imino]naphtho[1,2-d]thiazole hydrochloride;
2-(butylimino)-1,2-dihydro-1,4-dimethylnaphtho[1,2-d]thiazol-5-ol hydrochloride;
1,2-dihydro-1,4-dimethyl-2-(octylimino)naphtho[1,2-d]thiazol-5-ol hydrochloride;
1,2-dihydro-1,4-dimethyl-2-[2-phenylethyl)imino]-naphtho[1,2-d]thiazol-5-ol hydrochloride;
2[(3-acetylphenyl)imino]-1,2-dihydro-1,4-dimethylnaphtho[1,2-d]thiazol-5-ol;
5-hydroxy-4-methyl-2-(phenylimino)naphtho[1,2-d]thiazole-1 (2H)-ethanol hydrochloride;
9,10-dihydro-5-hydroxy-6-methyl-8H-imidazo[2,1-b]naphtho[1,2-d]thiazol-11-ium chloride;
8,9,10,11-tetrahydro-5-hydroxy-6-methyl-naphtho[1',2'4,5]thiazolo[3,2-α]pyrimidin-12-ium chloride.

Certain naphthothiazole derivatives of the above embodiment are novel, comprising those having the structure of

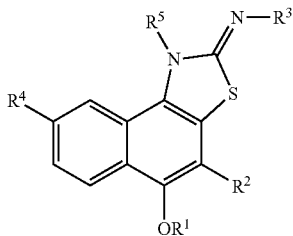

wherein
$R^1$ is selected from the group consisting of H, $C_{1-5}$ lower alkyl, $C_{1-18}$ lower alkanoyl, and aroyl;
$R^2$ is selected from the group consisting of hydrogen and $C_{1-6}$ lower alkyl;
$R^3$ is selected from the group consisting of lower alkyl, $C_3-C_5$ cycloalkyl, phenyl, 1-[(aminoiminomethyl)hydrazono]ethyl substituted phenyl, naphthyl, or the aminoalkyl group —A—$NR^6R^7$ wherein A is a straight or branched alkanediyl linker of 1–6 carbons and $R^6$ and $R^7$ are independently selected from the group consisting of hydrogen, $C_1$–$C_6$ alkyl, or $C_1$–$C_6$ hydroxyalkyl, or $R_6$ and $R^7$ taken together with the nitrogen atom form a $C_4$–$C_7$ heterocyclic ring optionally containing one or two additional heteroatoms selected from the group consisting of N, O or sulfur;
$R^4$ is selected from the group consisting of hydrogen, acetyl and 1-[(aminoiminomethyl)hydrazono]ethyl; and
$R^5$ is selected from the group consisting of hydrogen, $C_1$–$C_6$ alkyl, $C_1$–$C_6$ hydroxyalkyl, or aminoalkyl of structure —L—$NR^8R^9$ wherein L is a straight or branched alkanediyl linker of 1–6 carbons and $R^8$ and $R^9$ are independently selected from the group consisting of hydrogen, $C_1$–$C_6$ alky, $C_1$–$C_6$ hydroxyalkyl, or $R^8$ and $R^9$ taken together with the nitrogen atom form a $C_4$–$C_7$ heterocyclic ring optionally containing one or two additional heteroatoms selected from the group consisting of N, O or sulfur; with the proviso that if $R^4$ is hydrogen then $R^5$ is —L—$NR^8N^9$ as defined above;

or hydrochloride salts thereof, or other pharmaceutically acceptable salts thereof.

Representative naphthothiazoles of the above novel genus include, but are not limited to:

2-(cyclohexylimino)-1,2-dihydro-4-methyl-1-[3-(dimethylamino)propyl]naphtho[1,2-d]thiazol-5-ol dihydrochloride;
2-[[3-[1-[2-(aminoiminomethyl)hydrazono]ethyl]phenyl]amino]-4-methylnaphtho[1,2-d]thiazol-5-ol dihydrochloride;
4-methyl-2-[[3-(4-morpholino)propyl]amino]naphtho[1,2-d]thiazol-5-ol dihydrochloride;
8-[1-[2-(aminoiminomethyl)hydrazono]ethyl]-2-(butylimino)-1,2-dihydro-1,4-dimethylnaphtho[1,2-d]thiazol-5-ol monohydrochloride;
2-(Cyclohexylimino)-1,2-dihydro-4-methyl-1-[3-(4-morpholino)propyl]naphtho[1,2-d]thiazol-5-ol dihydrochloride;
2-(Cyclohexylimino)-1,2-dihydro-4-methyl-1-[3-(4-methyl-1-piperazinyl)propyl]naphtho[1,2-d]thiazol-5-ol trihydrochloride;

2-[[3-(Dimethylamino)propyl]imino]-1,2-dihydro-1,4-dimethylnaphtho[1,2-d]thiazol-5-ol dihydrochloride;

1,2-dihydro-1-[3-(dimethylamino)propyl]-4-methyl-2-[(1-methylethyl)imino]naphtho[1,2-d]thiazol-5-ol dihydrochloride;

1,2-dihydro-1-[3-(dimethylamino)propyl]-4-methyl-2-(phenylimino)naphtho[1,2-d]thiazol-5-ol dihydrochloride.

In a further embodiment, the composition of the present invention comprises one or more compounds of azinium derivatives of formula (III):

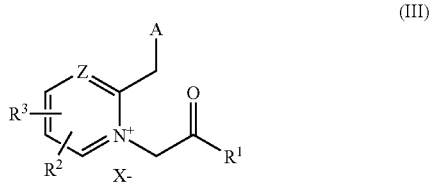

(III)

wherein A is hydrogen, cyano, or a $C_6$–$C_{10}$ aryl group, said aryl groups optionally substituted by one or more lower alkyl, lower alkoxy, or halo groups;

Z is CH or N;

$R^1$ is hydroxy, $C_1$–$C_{18}$ alkoxy, amino optionally substituted with 1–2 independent $C_1$–$C_{18}$ alkyl groups, phenyl, halosubstituted phenyl, $C_1$–$C_{18}$ alkoxysubstituted phenyl, or a $C_{4-7}$ aromatic or unsaturated or saturated heterocyclic ring having one to three heteroatoms selected from the group consisting of N, O, or S, with the proviso that at least one heteroatom is nitrogen and said nitrogen is directly bonded to the carbonyl group; and $R_2$ and $R_3$ are independently selected from hydrogen, amino, or $C_1$–$C_{18}$ alkyl groups, or $R_2$ and $R^3$ taken together may form a carbocyclic or heterocyclic ring, and $X^-$ is halide, preferably chloride or bromide, or other pharmaceutically acceptable anion.

A representative compound of the above embodiment known to the prior art is:

2-benzyl-1-(2-oxo-2-phenylethyl)pyridinium bromide.

Certain pyridinium derivatives of formula (III) are novel, as embodied in the structure

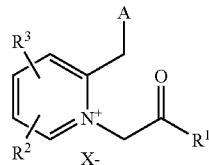

wherein
$R^1$ is selected from hydroxy, $C_1$–$C_{18}$ alkoxy, amino optionally substituted with 1–2 independent $C_1$–$C_{18}$ alkyl groups, phenyl, halosubstituted phenyl, $C_1$–$C_{18}$ alkoxysubstituted phenyl, or a heterocyclyl group defined as a 5 to 10 membered aromatic or unsaturated or saturated heterocyclic system of 1–2 rings having one or more heteroatoms selected from the group consisting of N, O, or S;
A is selected from the group consisting of hydroxy, $C_1$–$C_3$ hydroxyalkyl, cyano, phenyl, halosubstituted phenyl, $C_1$–$C_{18}$ alkoxysubstituted phenyl, a heterocyclyl group as defined for $R^1$ above with the proviso that the ring through which A is attached contains at least one heteroatom, or a group —C(=O)Z wherein Z is hydroxy, or Z is $C_1$–$C_{18}$ alkoxy, or Z is amino optionally substituted with 1–2 independent $C_1$–$C_{18}$ alkyl groups, or Z is heterocyclyl as defined for $R^1$ above;

$R^2$ and $R^3$ are independently selected from hydrogen, amino, or $C_1$–$C_{18}$ alkyl groups, or, if attached to adjacent ring positions, $R^2$ and $R^3$ taken together may form a carbocyclic or heterocyclic ring; and $X^-$ is halide, preferably chloride or bromide, or other pharmaceutically acceptable anion.
with the proviso that at least one of $R^1$ or A or Z is a heterocyclyl group as defined for the respective groups above.

Representative novel pyridinium compounds of the above embodiment include, but are not limited to:

1-[2-(1-pyrrolidinyl)-2-oxoethyl]-2-(cyanomethyl)pyridinium bromide;

1-[2-(1-pyrrolidinyl)-2-oxoethyl]-2-(cyanomethyl)pyridinium chloride; and

1-[2-(1-pyrrolidinyl)-2-oxoethyl]-2-benzylpyridinium bromide.

Furthermore, certain pyrimidinium derivatives of formula (III) are novel, as embodied in the structure

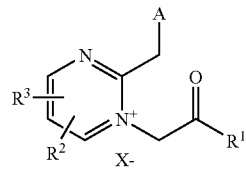

wherein
A is hydrogen, cyano, or a $C_6$–$C_{10}$ aryl group, said aryl groups optionally substituted by one or more lower alkyl, lower alkoxy, or halo groups;

Z is CH or N;

$R^1$ is hydroxy, $C_1$–$C_{18}$ alkoxy, amino optionally substituted with 1–2 independent $C_1$–$C_{18}$ alkyl groups, phenyl, halosubstituted phenyl, $C_1$–$C_{18}$ alkoxysubstituted phenyl, naphthyl, or a 4 to 10 membered aromatic heterocyclic or unsaturated heterocyclic or saturated heterocyclic ring system of 1 to 2 rings having one to three heteroatoms selected from the group consisting of N, O and S;

$R^2$ and $R^3$ are independently selected from hydrogen, amino, or $C_1$–$C_{18}$ alkyl groups, or $R^2$ and $R^3$ taken together may form a carbocyclic or heterocyclic ring, and $X^-$ is halide, preferably chloride or bromide, or other pharmaceutically acceptable anion;
with the proviso that if A is hydrogen, then $R^1$ is selected from phenyl, halosubstituted phenyl, $C_1$–$C_{18}$ alkoxysubstituted phenyl, or a 4 to 10 membered aromatic heterocyclic or unsaturated heterocyclic or saturated heterocyclic ring system of 1 to 2 rings having one to three heteroatoms selected from the group consisting of N, O and S.

Representative novel pyrimidinium compounds of the above embodiment include, but are not limited to:

2-methyl-3-(2-oxo-2-phenylethyl)-7-oxo-5,6,7,8-tetrahydropyrimidino[4,5-d]pyrimidin-3-ium bromide; and 1-(2-oxo-2-phenylethyl)-2,4,6-trimethylpyrimidinium bromide In another embodiment, the composition of the present invention comprises one or more compounds of N-aminopyrimidinium derivatives of formula (IV):

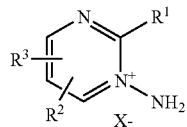

(IV)

wherein $R^1$ is selected from:
  amino,
  methyl,
  cyanomethyl,
  the group —$CH_2$—A where A is a $C_6$–$C_{10}$ aryl group optionally substituted by one or more lower alkyl, lower alkoxy or halo groups, or
  the group —$CH_2$—C(=O)Z where Z is selected from hydroxy, $C_1$–$C_{18}$ alkoxy, amino optionally substituted with 1–2 $C_1$–$C_{18}$ alkyl groups, a $C_6$–$C_{10}$ aryl group optionally substituted by one or more lower alkyl or halo groups, or a $C_{4-7}$ aromatic or unsaturated or saturated heterocyclyl group having one to three heteroatoms selected from the group consisting of N, O, or S;
$R^2$ and $R^3$ are independently selected from hydrogen, amino, lower alkoxy, or $C_1$–$C_8$ alkyl groups, or if $R_2$ and $R_3$ are on adjacent atoms then $R^2$ and $R^3$ taken together with their ring atoms may form a fused carbocyclic or heterocyclic ring; and
$X^-$ is mesitylene-2-sulfonate or other pharmaceutically acceptable anion.

Representative compounds of the above embodiment known in the prior art include:
1,2-diaminopyrimidinium mesitylene-2-sulfonate; and
1,6-diamino-4-methoxy-2-methylpyrimidinium mesitylene-2-sulfonate.

Certain N-aminopyrimidinium derivatives of formula (IV) are novel, as embodied in the structure

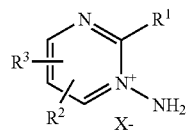

wherein
  $R^1$ is selected from:
    amino,
    methyl,
    cyanomethyl,
    the group —$CH_2$—A where A is a $C_6$–$C_{10}$ aryl group optionally substituted by one or more lower alkyl, lower alkoxy or halo groups, or
    the group —$CH_2$—C(=O)Z where Z is selected from hydroxy, $C_1$–$C_{18}$ alkoxy, amino optionally substituted with 1–2 $C_1$–$C_{18}$ alkyl groups, a $C_6$–$C_{10}$ aryl group optionally substituted by one or more lower alkyl or halo groups, or a 4 to 10 membered aromatic heterocyclic or unsaturated heterocyclic or saturated heterocyclic ring system of 1 to 2 rings having one to three heteroatoms selected from the group consisting of N, O and S;
  $R^2$ and $R^3$ are independently selected from hydrogen, amino, $C_1$–$C_6$ alkoxy, or $C_1$–$C_8$ alkyl groups, or if $R^2$ and $R^3$ are on adjacent atoms then $R^2$ and $R^3$ taken together with their ring atoms may form a fused carbocyclic or heterocyclic ring; and
  $X^-$ is mesitylene-2-sulfonate or other pharmaceutically acceptable anion.

Representative novel N-aminopyrimidinium compounds of the above embodiment include, but are not limited to:
1,2-diamino-4-methylpyrimidinium mesitylene-2-sulfonate;
1,2-diamino-6-methylpyrimidinium mesitylene-2-sulfonate;
1,2-diamino-4,6-dimethylpyrimidinium mesitylene-2-sulfonate, mp 242–243 C;
1,6-diamino-2,4-dimethylpyrimidinium mesitylene-2-sulfonate;
1,4-diamino-2,6-dimethylpyrimidinium mesitylene-2-sulfonate;
1-amino-2,4,6-trimethylpyrimidinium mesitylene-2-sulfonate, mp183–185 C; and
2-methyl-3-amino-7-oxo-5,6,7,8-tetrahydropyrimidino[4,5-d]pyrimidin-3-ium mesitylene-2-sulfonate.

In yet another embodiment, the composition of the present invention comprises one or more compounds of imidazolium derivatives of formula (V):

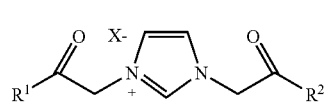

(V)

wherein $R^1$ and $R^2$ are independently selected from hydroxy, lower alkoxy, amino optionally substituted with 1–2 lower alkyl groups, aryl, halosubstituted aryl, (lower alkyl)substituted aryl, or a $C_{5-7}$ unsaturated or saturated heterocyclic ring having one to three heteroatoms selected from the group consisting of N, O, and S and $X^-$ is halide, preferably chloride or bromide, or other pharmaceutically acceptable anion.

Compounds of the above embodiment known to the prior art include, but are not limited to:
1,3-bis(2-oxo-2-phenylethyl)imidazolium bromide;
1,3-bis[2-oxo-2-(4-methylphenyl)ethyl]imidazolium bromide;
1,3-bis[2-oxo-2-(2,3,5,6-tetramethylphenyl)ethyl]imidazolium bromide;
1,3-bis[2-oxo-2-(4-chlorophenyl)ethyl]imidazolium bromide;
1,3-bis[2-oxo-2-(3,4-dihydroxyphenyl)ethyl]imidazolium bromide;
1,3-bis[2-oxo-2-(4-biphenylyl)ethyl]imidazolium bromide;
1,3-bis(2-oxopropyl)imidazolium chloride;
1,3-bis(2-oxo-2-ethoxyethyl)imidazolium chloride;
1-(2-oxo-2-methoxyethyl)-3-[2-oxo-2-(3-methoxyphenyl)ethyl]imidazolium bromide.

Certain imidazolium compounds of formula (V) are novel, as embodied in the structure

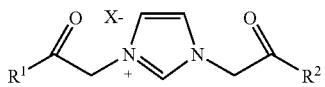

wherein
R¹ and R² are independently selected from hydroxy, $C_1$–$C_{18}$ alkoxy, amino optionally substituted with 1–2 independent alkyl groups of 1–8 carbons, aryl, halo-substituted aryl, (lower alkyl)substituted aryl, or a heterocyclyl group defined as a 4 to 10 membered aromatic heterocyclic or unsaturated heterocyclic or saturated heterocyclic ring system of 1 to 2 rings having one to three heteroatoms selected from the group consisting of N, O and S, with the proviso that one of $R_1$ or $R_2$ must be an optionally substituted amino group or heterocyclyl group as defined above;

$X^-$ is halide, preferably chloride or bromide, or other pharmaceutically acceptable anion;

Representative novel compounds of the above embodiment include, but are not limited to:

1,3-bis[2-oxo-2-(1-pyrrolidinyl)ethyl]imidazolium chloride;
1,3-bis[2-oxo-2-(2-thienyl)ethyl]imidazolium bromide;
1-(2-oxo-2-phenylethyl)-3-[2-oxo-2-(1-pyrrolidinyl)ethyl] imidazolium bromide;
1-(2-oxo-2-phenylethyl)-3-[2-oxo-2-(2-thienyl)ethyl]imidazolium bromide; and
1-[2-oxo-2-(2-thienyl)ethyl]-3-[2-oxo-2-(1-pyrrolidinyl) ethyl]imidazolium bromide.

For the purposes of this invention, the compounds of the present invention are formed as biologically and pharmaceutically acceptable salts. Useful salt forms are the halides, particularly the bromide and chloride, tosylate, methanesulfonate, and mesitylene-2-sulfonate salts. Other related salts can be formed using similarly non-toxic, and biologically and pharmaceutically acceptable anions.

Unless otherwise specified, the alkyl groups referred to above contain one to about eighteen carbon atoms and include, for example, methyl, ethyl, propyl, butyl, pentyl, hexyl, octyl, decyl, dodecyl, and octadecyl, and the corresponding branched-chain isomers thereof. Lower alkyl groups, of one to about six carbon atoms, are preferred. The alkyl groups optionally substituted by hydroxy groups include alkyl groups as hereinbefore defined substituted with a hydroxy group at any position, such as but not limited to the following examples: hydroxymethyl, 1-hydroxyethyl, 2-hydroxyethyl, 1-hydroxypropyl, 2-hydroxypropyl, 3-hydroxypropyl, 6-hydroxyhexyl, and the like. Hydroxy-substituted lower alkyl groups as defined above are preferred. Similarly, unless otherwise specified, the alkoxy groups contain from one to about eighteen carbon atoms, and include, for example, methoxy, ethoxy, propoxy, butoxy, pentyloxy, hexyloxy, decyloxy, and octadecyloxy, and the corresponding branched-chain isomers thereof. Lower alkoxy groups of one to about 6 carbons, are preferred. The alkanoyloxyalkyl groups encompassed by the above formula include those wherein the alkanoyl portion contains from one to about eighteen carbon atoms and the alkyl portion contains from 1 to about eighteen carbon atoms. Typical alkanoyloxy portions are those such as acetoxy or ethanoyloxy, propanoyloxy, butanoyloxy, pentanoyloxy, hexanoyloxy, decanoyloxy, and octadecanoyloxy, and the corresponding branched chain isomers thereof. The preferred alkyl portions of these molecules have from one to about six carbon atoms.

In one embodiment, a composition comprising one or more compounds of Formulas I through V and/or any combination thereof of the present invention may be used for in vivo treatment of protein masses or other biomaterials of the body, among them collagen, elastin, lens proteins, the kidney glomerular basement membrane, nucleic acids and lipids. The compositions have utility in vivo to reduce the deleterious effects of sugar-mediated coupling in an organism, when the organism is exposed to the compound or composition internally, by ingestion, or other means.

The compositions of the present invention comprising the above disclosed compounds are capable of uncoupling sugar-mediated coupling of proteins, lipids, nucleic acids, and other biomaterials, and any combination thereof. The sugar-mediated coupling of proteins or other biomaterials contributes to the entrapment of other proteins or biomaterials and results in the development in vivo of conditions such as reduced elasticity and wrinkling of the skin, certain kidney diseases, atherosclerosis, osteoarthritis and the like. Similarly, foodstuffs including plant and animal material that undergoes nonenzymatic browning deteriorates and becomes spoiled or toughened and, consequently, inedible, unpalatable or non-nutritious. Thus, the compounds employed in accordance with this invention uncouple sugar-mediated coupling of proteins, lipids, nucleic acids, and other biomaterials, and any combination thereof. Consequently, the present methods and compositions may be used to reverse the aging of key proteins and other biomaterials both in animals and plants, and concomitantly, to confer both economic and medical benefits as a result thereof. In the instance of foodstuffs, the administration of the present composition may be used to reduce the physico-chemical changes imparted to foodstuffs on storage, such as the increased toughness of meats that occurs during aging or storage.

The therapeutic implications of the present invention relate to the reduction of the aging process which occurs by the aging of key proteins and other biomaterials by sugar-mediated coupling. Thus, body proteins, and particularly structural body proteins, such as collagen, elastin, lens, proteins nerve proteins, kidney glomerular basement membranes and other biomaterials and extravascular matrix components would all benefit in their longevity and operation from the practice of the present invention. The present invention thus reduces the incidence of pathologies involving the entrapment of proteins and other biomaterials by uncoupling of sugar-mediated coupling of proteins, lipids, nucleic acids, and other biomaterials, and any combination thereof, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, urinary incontinence and obstruction, coronary artery disease, presbyacusis, presbyopia, pulmonary disease etc. Likewise, all of these conditions are in evidence and tend to occur at an accelerated rate in patients afflicted with diabetes mellitus as a consequence of their hyperglycemia. Thus, the present therapeutic method is relevant to treatment of these and related conditions in patients either of advanced age or those suffering from one of the mentioned pathologies.

Sugar-mediated coupling can decrease solubility of structural proteins such as collagen in vessel walls and can also trap serum proteins, such as lipoproteins to the collagen. Also, the presence of sugar-mediated coupling may result in increased permeability of the endothelium and consequently covalent trapping of extravasated plasma proteins and other biomaterials in subendothelial matrix, as well as a reduction in susceptibility of both plasma and matrix proteins and other biomaterials to physiologic degradation by enzymes. For these reasons, the progressive occlusion of diabetic vessels induced by chronic hyperglycemia has been hypothesized to result from excessive formation of sugar-mediated coupling. Such diabetic microvascular changes and microvascular occlusion can be effectively reduced by the uncoupling of sugar-mediated coupling of proteins, lipids, nucleic acids, and other biomaterials, and any combination thereof utilizing a composition and the methods of the present invention.

Table 1 below is an illustrative list of various types of organ systems that may be treated in vivo with the composition and method of the present invention. This list is merely illustrative and should not be construed as limiting the invention.

| Organ System | Primary Disease Classification | Specific Examples |
|---|---|---|
| General | Age-related, degenerative | Amyloidosis<br>Scleroderma<br>Autoimmune diseases |
| Cardiovascular | Age-related, degenerative | Isolated Systolic HTN<br>Idiopathic cardiomyopathy |
| | Vascular (atherosclerosis-related) | Congestive heart failure<br>Coronary artery disease |
| | Diabetes-related | Myocardial Infarction<br>Peripheral vascular disease<br>Stroke<br>Ischemic cardiomyopathy<br>Diastolic dysfunction (LV) |
| Pulmonary | Age-related, degenerative | Alveolo-capillary block<br>COPD |
| | Vascular (atherosclerosis-related) | Idiopathic fibrosis<br>Secondary pulmonary HTN |
| | Diabetes-related | Pulmonary fibrosis |
| Central Nervous | Age-related, degenerative | Dementia (senile, Alzheimer) |
| | Vascular (atherosclerosis-related) | Prion-related diseases<br>Dementia (post-infarction) |
| | Diabetes-related | Metabolic encephalopathies |
| Peripheral Nervous | Age-related, degenerative | Infiltrative neuropathy<br>Polyneuropathies |
| | Vascular (atherosclerosis-related) | Diabetic neuropathy |
| | Diabetes-related | |
| Gastrointestinal | Age-related, degenerative | Diverticulosis<br>Esophageal diverticulum |
| | Vascular (atherosclerosis-related) | Hiatal hernia<br>Constipation |
| | Diabetes-related | Ischemic gastroenteropathies<br>Diabetic gastroenteropathies |
| Hepatic | Age-related, degenerative | Cirrhosis<br>Infiltrative hepatic diseases |
| | Vascular (atherosclerosis-related) | Ischemic hepatic disease |
| Genitourinary | Age-related, degenerative | Incontinence<br>Obstruction |
| | Vascular (atherosclerosis-related) | Erectile dysfunction<br>Renal failure |
| | Diabetes-related | Peritoneal dialysis<br>Ischemic vesiculopathies<br>Incontinence<br>Obstruction |
| Musculoskeletal | Age-related, degenerative | Muscle stiffness<br>Bone brittleness |
| | Diabetes-related | Muscle weakness |
| Hematological | Age-related, degenerative | Myelofibrosis<br>Lymphedema |
| | Diabetes-related | Splenomegaly |
| Dermal | Age-related, degenerative | Decreased RBC deformability<br>Wrinkles, loss of skin elasticity |
| | Vascular (atherosclerosis-related) | Scleroderma<br>Dermatomyositis |
| | Diabetes-related | Accelerated ageing<br>Scleredema |
| Endocrine | Age-related, degenerative | Gonadal failure<br>Hormone resistance |
| | Diabetes-related | Increased diffusion barrier |
| Reproductive | Age-related, degenerative | Infertility<br>Infertility |
| | Vascular (atherosclerosis-related) | Infertility |
| | Diabetes-related | |
| Ophthalmic | Age-related, degenerative | Presbyopia<br>Glaucoma |
| | Vascular (atherosclerosis-related) | Macular degeneration (age-related) |
| | Diabetes-related | Diabetic retinopathy |
| Hearing | Age-related, degenerative | Presbyacusis<br>Hearing loss |
| | Vascular (atherosclerosis-related) | Senso-neuronal hearing loss |
| | Diabetes-related | |
| Renal | Age-related, degenerative | Glomerusclerosis<br>Hypertensive nephropathy |
| | Vascular (atherosclerosis-related) | Diabetic nephropathy |
| | Diabetes-related | |

In the instance where the compositions of the present invention are utilized for in vivo or therapeutic purposes, it may be noted that the compounds or agents used therein are biocompatible. Various biologically or pharmaceutically acceptable salts may be used, such as halides, tosylate, etc. Pharmaceutical compositions may be prepared with a therapeutically effective quantity of the compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of the present invention may be utilized.

In another embodiment, a liquid form may be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the compound in a suitable vehicle such as water, ethanol, propylene glycol, perhaps including a carrier to aid in penetration into the skin or eye. For example, a topical preparation could include up to about 10% of the disclosed compounds. Other suitable forms for administration to other body tissues are also contemplated.

In the instance where the present method has therapeutic application, the human or animal host intended for treatment may have administered to it a quantity of one or more of the compounds, in a suitable pharmaceutical form. Administration may be accomplished by known techniques, such as oral, topical and parenteral techniques such as intradermal, subcutaneous, intravenous or intraperitoneal injection, as well as by other conventional means. Administration of the compounds may take place over an extended period of time at a dosage level of, for example, up to about 30 mg/kg.

In a further embodiment of the present invention, the compositions have utility in treatment of proteinaceous organism-derived materials of commerce comprising fur, leather, feathers, down, silk, wool, gut, or the like, to enhance their softness and suppleness of texture and reduce their stiffness and brittleness, thus increasing the value and functionality of such materials. Such treatment is accomplished by exposing the organism-derived material to a solution of the composition at a concentration of 0.1–5.0% or preferably 0.25–2.0% in water or other suitable solvent such as ethanol, ethylene glycol, or propylene glycol, or mixtures of such solvents. The organism-derived material is then drained or filtered to remove the solution, rinsed with water and air-dried.

In a further embodiment, the present invention relates to methods for treating hair and nails and ex-vivo treatment of organs, cells and tissues that comprise contacting the targeted area with a composition comprising the compounds of the present invention. Various changes in the biomechanical and other functional properties of hair may occur with aging and diseases. Undesirable changes may include deterioration in manageability, including decreased stability and brittle hair. Typically, these detrimental changes may be due to: (a) physically or chemically damaged hair; (b) physiologically aged hair; and/or (c) diseased hair (e.g. hair of diabetics). Hair may also be physically damaged from the normal grooming process of shampooing, combing, drying (e.g. hot air blow drying), and brushing. In addition to this physical damage of hair, hair may also be damaged by chemical action such as by exposure to sunlight and contact with water containing chemically reactive agents such as oxidizers (e.g bleaching and/or dyeing of hair). Also, the repeated use of permanent waving compositions on the hair fibers may cause damage to the hair especially if not used according to directions. Bleached hair is often characterized as being dry, brittle, and overly coarse. Finally, with the aging process, hair may become dry, brittle and overly coarse.

For nails, deterioration in the biomechanical and other functional properties may also result in undesirable nail problems. Conventionally, the term "nail" has meant the horny cutaneous plate on the dorsal surface of the distal end of a finger or toe, or the corresponding appendages in animals. Specifically, in humans, the hardness and strength of the nails is particularly important not only for the beauty of their appearance, but for the well-being of the individual. Embrittlement of the nails is normally associated with aging. However, various activities also expose nails to a number of materials which may adversely affect the nail's biomechanical and other functional properties. For example, occupational exposure to extensive or constant wetting of the hands with soaps, detergents, solvents, chemical hair waving and coloring lotions, and insults from deliberate cosmetic applications, such as manicuring, or any like products can lead to drying, brittleness, cracking, laminating, splitting, ridging and similar damage. Additionally, certain diseases may also lead to nail embrittlement or associated disfigurement owing to weakening of nail hardness and strength. Moreover, the appearance of fingernails and toenails of humans are frequently enhanced with decorative nail-care cosmetics, such as nail polishes, nail polish removers, nail polish bases, alkaline cuticle removers and the like. Overuse of these products can alter the nail, causing it to weaken, soften, split and break.

In an embodiment, for topical application to hair or nails, a solution, a lotion or ointment may be formulated with the compound in a suitable vehicle such as water, ethanol, propylene glycol, perhaps including a carrier to aid in contacting the hair or nails. For example, a topical preparation could include up to about 10% of the compounds of Formulas I through V and/or any combination thereof. Other suitable forms for administration to other body tissues are also contemplated.

In another embodiment of the present invention, a method and composition are disclosed for the "rejuvenation" of hair, nails, tissues, cells and organs by ex-vivo treatment. In particular, a composition comprises one or more compounds of Formulas I through V and/or any combination thereof for ex-vivo treating hair, nails, tissues, cells and organs to improve the biomechanical and other functional properties of hair, nails, tissues, cells and organs. More particularly, for hair and nails, the composition and method of the present invention comprises compounds for rejuvenating: (a) damaged hair or nails; (b) physiologically aged hair or nails; and/or (c) diseased hair or nails (e.g. diabetes). For cells, tissues and organs, the composition and method of the present invention comprise one or more compounds of Formulas I through V and/or any combination thereof for rejuvenating tissues, cells and organs by improving the deformability and/or diffusion coefficient of tissues, cells and organs from a state of decreased deformability and impaired diffusional characteristics, as typically observed in cells, tissues or organs of older individuals, to a state of increased deformability and improved diffusional characteristics, as commonly seen in cells, tissues and organs of healthy and young individuals (i.e 20 years old).

The compound of Formula (I), (II), (III), (IV), or (V) or any combinations thereof is formulated in a composition in an amount effective to return the biomechanical and diffusional characteristics of the sample to the state typical of that found in a healthy 20 year old human. This amount will, of course, vary with the particular agent being utilized and the particular dosage form, but typically is in the range of 0.01% to 1.0%, by weight, of the particular formulation.

In one embodiment relating to the treatment of hair, one or more compounds of Formulas I through V and/or any combination thereof may be combined with other components to form a composition that may be used to treat: (a) damaged hair; (b) physiologically aged hair; and (c) diseased hair (e.g. diabetes). The compositions of the present invention may be compounded and/or mixed with shampoo compositions containing, anionic, nonionic and cationic surfactants, as well as hair conditioning compositions. In yet another embodiment, the compositions of the present invention may be incorporated with conventional hair treating compositions such as bleaching compositions, hair dyeing compositions and/or hair relaxers.

In an embodiment that includes a hair treatment composition of the present invention, surface active agents may be used and include, but are not limited to, coconut oil fatty acids or oleic acid, alkali metal or ammonium or amine soaps, water-soluble lauryl sulfate salts, usually alkali metal, ammonium and ethanolamine, commonly diethanolamine or triethanolamine, salts; alkanolamine salts of linear $C_{12}$–$C_{15}$ alkyl benzene sulfonic acids; water-soluble polyethoxylauryl alcohol sulfate salts; linear alkyl benzene polyoxyethyl sulfonate salts; sulfated lauric acid monoglyceride salts; quaternary ammonium compounds such as cetyltrimethyl ammonium chloride; nonionic detergents such as octylphenoxypoly(ethyleneoxy)ethanol; and amphoteric detergents.

In a further embodiment, a shampoo composition of the present invention may include foam boosters or foam stabilizers. Such boosters include, but are not limited to, dialkylolamides of $C_8$–$C_{18}$ fatty acids, as, for instance, lauric or cocodiethanolamides which are represented by the formula R—CO—N—$(CH_2$—$CH_2$—$OH)_2$ where R—CO is a saturated fatty acid acyl radical of $C_8$–$C_{15}$ fatty acids, particularly lauric acid or myristic acid or mixtures of saturated fatty acids containing predominately from $C_{12}$ to $C_{14}$ fatty acids and commonly derived from coconut oil.

In one embodiment, the composition for treating hair may be adjusted to a pH from about 6 to about 9, more particularly from about 5.5 to about 7.5.

In a further embodiment, the composition for treating hair may include supplemental ingredients for particular purposes such as polymers, combing aids, etc.—liquids, gels, creams or dry powders.

In an embodiment relating to the treatment of nails, one or more compounds of Formulas I through V and/or any combination thereof may be combined with conventional nail polish components to form a composition that may be used to treat: (a) damaged nails; (b) physiologically aged nails; and (c) diseased nails (e.g. diabetes). The nail polish compositions of the present invention may include various solvents, resins, FDA certified pigments, and pigment extenders. The following are illustrative examples of each of these components. For example, solvents may include n-butyl acetate (ester solvent), ethyl acetate (ester solvent), propylene glycol methyl ether acetate (ester solvent), isopropyl alcohol (oxygenated solvent), dipropylene glycol methyl ether (glycol ether solvent), naphtha/petroleum naphtha (aliphatic petroleum solvent) mineral spirits (aliphatic petroleum solvent). For example, resins may include acrylic resin (a polymer of acrylic-methacrylic acids and their esters), maleated-rosin (rosin-maleic adduct), nitrocellulose (soluble cellulose ester), pigment. In addition, FD&C colors and/or FDA certified pigments may be used. In a further embodiment, pigment extenders may be used such as magnesium silicate (Vantac 6H), silicone dioxide (amorphous silica), aluminum stearate, calcium carbonate, barium sulfate, aluminum silicate, calcium silicate and calcium sulfate.

In a further embodiment, the composition of the present invention may include antifungal agents such as miconazole nitrate, ketoconazole, itraconazole, fluconazole, econazole, terconazole, saperconazole, amorolfine, ciclopirox, oxiconazole, clotrimazole, terbinafine, naftifine, and other antifungal drugs that are available in a topical formulation. In addition, the formulation containing the antifungal drug may include an agent such as hydroxypropyl-alpha-cyclodextrin that enhances the water-solubility of the antifungal drug. The anti-fungal drugs are used in anti-fungally effective amounts. For example, anti-fungally effective amounts are usually from about 0.5% to about 10%, by weight, and more particularly from about 1% to about 5%, by weight, of the formulation that is applied to the nail or surrounding dermal tissue.

In another embodiment, one or more compounds of Formulas I through V and/or any combination thereof may be applied in the area of tissue "rejuvenation". For purposes of the present invention, the terms "cells", "tissues" and "organs" may be used interchangeably as organs consist of tissue and tissue contain cells and extracellular material. The term "rejuvenation" means sufficiently improving the deformability and/or diffusion coefficient of cells, tissues and/or organs from a state of decreased deformability and impaired diffusional characteristics, as typically observed in cells, tissues or organs of older individuals, to a state of increased deformability and improved diffusional characteristics, as commonly seen in cells, tissues and organs of healthy and young individuals (e.g., 20 years old). One method of determining whether the cells, tissues or organs have been "rejuvenated" is whether, after treatment with the compositions of the present invention, the biomechanical and diffusional characteristics of the treated cells, tissues or organs have been changed by at least 20% toward the characteristics of a healthy 20 year old human.

Decreased deformability is associated with impaired tissue or organ functionality in itself, as optimal biomechanical function is demonstrated at deformability levels measured in healthy and young individuals and diminishes with progressively decreasing levels of deformability. It is believed that the aging process, in addition to modifying the deformability, also induces additional specific impairments in the functionality of cells, tissues and/or organs that are not directly related to deformability. It is further believed that this impairment in functionality is related to an altered diffusion coefficient of molecules across intracellular and extracellular spaces. The decreased ability of molecules to traverse intra- and extracellular spaces may affect signaling functions of hormones and cytokines, transportation of oxygen and nutrients from the vascular space to the cell, and cellular metabolism.

Table 2 below is an illustrative list of various types of ex-vivo tissues, ex-vivo cells and ex-vivo organs that may be treated with the composition and method of the present invention. This list is merely illustrative and should not be construed as limiting the invention.

TABLE 2

| Cells | Tissues | Organs |
| --- | --- | --- |
| Beta cells of pancreas | Tendons | Heart |
| Cardiac myocytes | Ligaments | Lungs |
| Neurons | Bone | Kidneys |
| Macrophages | Vessels | Liver |
| Erythrocytes | Cardiac valves | Spleen |
| Leukocytes | Cornea | Adrenals |
| Fibrocytes | Muscle | Gonads |
|  | Skin Appendages | Skin |
|  | Cartilages | Pituitary |
|  | Trachea | Gastrointestinal |
|  |  | Eyes |
|  |  | Hearing Apparatus |

For purposes of the present invention, "rejuvenation" will be measured by one or more of the techniques to measure deformability and/or other functionality of tissues, cells or organs. Commonly used methods to determine deformability include ultrasonographic techniques and the determination of volume-pressure and stress-strain relationships, but are not limited to these. Table 3 is an illustrative list of some of the currently available measures used for evaluating aspects of deformability: This list is merely illustrative and should not be construed as limiting the techniques that may be used to measure the deformability of tissues, cells or organs.

TABLE 3

|  | Cells | Tissues | Organs |
| --- | --- | --- | --- |
| In vitro | Membrane deformability | Compliance | Compliance |
|  |  | Distensibility | Distensibility |
|  |  | Impedance | Impedance |
|  |  | Tensile strength | Wall tension |
|  |  | Wall tension | Compressive strength |
|  |  | Compressive strength | Flexibility |
|  |  | Flexibility | Torsion |

TABLE 3-continued

| Cells | Tissues | Organs |
|---|---|---|
| | Torsion | Elasticity |
| | Elasticity | Viscoelasticity |
| | Viscoelasticity | Shear |
| | Shear | |
| In vivo Membrane deformability | Compliance | Compliance |
| | Distensibility | Distensibility |
| | Impedance | Impedance |
| | Wall tension | Wall tension |
| | Flexibility | Flexibility |
| | Elasticity | Elasticity |
| | Viscoelasticity | Viscoelasticity |

Another method of determining the degree of "rejuvenation" for the present invention is to measure the diffusion coefficient of molecules across intracellular and extracellular spaces. Methods used to measure the diffusion coefficient of molecules across intracellular and extracellular spaces include the determination of the reaction time of biomolecular feed-back mechanisms based on the diffusion of molecules across a cellular, tissue and/or organ space to reach a target response element and the measurement of the diffusion rate of certain molecules across biological spaces or the diffusion rate of tracer molecules like dyes or radioisotopes. Examples of methods to determine the biomolecular feedback mechanisms include, but are not limited to, the following: (a) hypothalamic-pituitary axis: growth hormone, ACTH, TSH, or prolactin; (b) pituitary-adrenal axis: cortisol; (c) pituitary-thyroid axis: thyroxin; and (d) pituitary-gonadal axis: sex hormones, LH, and FSH. Examples of methods to determine the diffusion rate of certain molecules across biological spaces include, but are not limited to, the following: arterio-alveolar oxygen and carbon dioxide gradients; insulin resistance; and arteriovenous oxygen gradient (e.g., heart, muscle).

In one embodiment, one or more compounds of Formulas I through V and/or any combination thereof of the present invention may be combined with a pharmacologically acceptable organ storage solution that results in a rejuvenation solution. The solution of the present invention may be utilized to rejuvenate major organs such as the kidney, heart, pancreas, liver, lungs and intestines and portions or segments thereof. In another embodiment, organs may be rejuvenated by flushing the organ after it has been removed from a cadaver with the rejuvenation solution of the present invention followed by cold storage of the organ in the rejuvenation solution at temperatures of about 4° C. Organs stored in the rejuvenation solution may then be transplanted into an appropriate transplant recipient.

Furthermore, with respect to tissues, cells and organs, it is noteworthy that transplantation of these materials has become a routine means of treating certain diseases and other conditions. Transplantation requires a ready source of organs, such as kidney, pancreas, liver, heart, etc., from living persons or cadavers. Conventionally, most vital organs, cells and tissues, which are used for transplantation, are obtained from heart beating cadavers and preserved for variable periods of time prior to their transplantation. However, preservation methods merely attempt to maintain the present condition of the organ, cell or tissue. For this reason, the majority of organs, cells and tissues that are used for transplantation presently come from younger individuals who typically have tissues, cells and organs that have not been detrimentally affected by age or disease.

In contrast, because of the aging process or disease, older individuals have a deterioration in the biomechanical (e.g. deformability) and other functional properties of their cells, tissues and organs. For this reason, decreased deformability is associated with impaired tissue or organ functionality in itself, as optimal biomechanical function is demonstrated at deformability levels measured in young individuals and diminishes with progressively decreasing levels of deformability. Thus, at the present time, older individuals typically can not be candidates for organ, tissue or cell donation because preservation solutions merely attempt to preserve the present condition of the organ, cell or tissue.

Conventionally, two typical methods of preserving organs, cells and tissues for transplantation are continuous pulsatile perfusion and simple hypothermic storage in a preservation solution. In pulsatile perfusion, the organ is subjected to pulsatile flow of a perfusate under hypothermic conditions such that the organ membranes receive sufficient oxygenation. Typically, the perfusate contains albumin and lipids. With simple hypothermic storage, organs are removed from a cadaver donor and rapidly cooled. Rapid cooling is achieved by external cooling and by perfusion with a preservation solution to lower the internal temperature of the organ. The organ is then stored immersed in the preservation solution at temperatures of about 0°–4° C. Two conventional glucose preservation flush solutions are the Collins (G. M. Collins, The Lancet, 1969, 1219–1222) and the Euro-Collins (J. P. Squifflet et al, Transplant. Proc., 1981, 13:693–696) solutions. These solutions resemble intracellular fluid and contain glucose as an osmotic agent. Despite their widespread use, the Collins and Euro-Collins preservation solutions do not typically provide adequate preservation for storage times greater than about 48 hours. For example, kidneys stored in Collins solution for 24 hours may exhibit considerable damage to the nephrons. This damage included degradation of cells lining the proximal tubules, extensive swelling and rupturing of cells lining the ascending distal tubules, degeneration of glomerular epithelial and endothelial cells and accumulation of flocculent cytoplasmic debris in the capsular spaces of Bowman. (P. M. Andrews et al, Lab. Invest., 1982, 46:100–120). In addition to glucose flush solutions, high osmolality preservation solutions have been prepared using raffinose and lactobionate as in the UW preservation solution (R. J. Ploeg et al, Transplant. Proc., 1988, 20 (suppl 1) 1:935–938), mannitol in the Sacks solution (S. A. Sacks, The Lancet, 1973, 1:1024–1028), sucrose in the phosphate buffered sucrose (PBS) preservation solution (F. T. Lam et al, Transplantation, 1989, 47:767–771) and the histidine buffered HTK solution of Bretschneider (N. M. Kallerhoff et al, Transplantation, 1985, 39:485–489). Other examples are solutions that contain synthetic hydroxyethyl starch (HES) as an osmotic colloid.

The rejuvenation solution of the present invention may be a pharmacologically acceptable solution such as an aqueous buffer solution containing any of the specific compounds claimed. In one embodiment, an aqueous phosphate buffer may be prepared, for example, by mixing sodium hydrogen phosphate ($Na_2HPO_4$) and sodium dihydrogen phosphate ($NaH_2PO_4$) in water preferably; the water should be purified by distillation, deionization, etc. prior to use. In a further example, if a cardioplegic solution for rejuvenation of hearts is desired, a phosphate buffer solution may be prepared using potassium hydrogen phosphate ($K_2HPO_4$) and/or potassium dihydrogen phosphate ($KH_2PO_4$).

In a further embodiment, the rejuvenation composition of the present invention may be adjusted to have a pH of 7.0 or greater; more particularly in the range of 7.1–7.4.

In another embodiment, the rejuvenating solutions of the present invention may contain an osmotic agent. Suitable conventional osmotic agents include any osmotic agent known for use in preservation solutions, including mannitol, sucrose, raffinose, and lactobionate. The osmotic agent is added to the rejuvenating solution in a sufficient amount to provide adequate osmolality and rejuvenation properties.

In yet another embodiment, the rejuvenating solution of the present invention may contain other components which do not adversely affect the rejuvenating properties of the solution. For example, addition of glutathione or a $C_{1-6}$ alkyl glutathione monoester (M. E. Anderson et al, Arch. Biochem. Biophys., 1985, 239:538–548, ethyl ester) in amounts of about 210 mmol/l.

In a further embodiment, a suitable hypothermic solution, such as the solution formulated by the University of Wisconsin, that may be combined with the compositions of the present invention to rejuvenate the kidney, is composed of Sodium (30 mmol $L^{-1}$), Potassium (125 mmol $L^{-1}$), Magnesium (5 mmol $L^{-1}$), Sulphate (5 mmol $L^{-1}$), Lactobionate (100 mmol $L^{-1}$), Phosphate (25 mmol $L^{-1}$), Raffinose (30 mmol $L^{-1}$), Adenosine (5 mmol $L^{-1}$), Gluthatione (3 mmol $L^{-1}$), Allopurinol (1 mmol $L^{-1}$), Insulin (100 units $L^{-1}$), Dexamethasone (8 mg $L^{-1}$), Bactrim (0.5 ml), HES (50 g $L^{-1}$), Osmolality (320 mmol $kg^{-1}$), and pH of 7.4.

Further embodiments of suitable cold storage solutions that may be combined with the compositions of the present invention to rejuvenate the kidney comprise the Collins solution (Collins, B M, Lancet 1969;2:1219) and the Euro-Collins solution (Squifflet J P, Transplant Proc 1981;13: 693). Examples of further embodiments of suitable preservation solutions that may be combined with the compositions of the present invention to rejuvenate the heart comprise the aforementioned University of Wisconsin solution, the Stanford solution (Stein D G, J Thorac Cardiovasc Surg 1991;102:657) and the St. Thomas' solution (Demertzis S, Ann Thorac Surg 1993;55:1131).

Examples of further embodiments of suitable pneumoplegia solutions that may be combined with the compositions of the present invention to rejuvenate the lung comprise the Euro-Collins and the University of Wisconsin solutions.

In a further embodiment, a suitable preservation solution that may be combined with the compositions of the present invention to rejuvenate a liver is the Euro-Collins solution. In yet a further embodiment, a suitable preservation solution that may be combined with the compositions of the present invention to rejuvenate a liver consists of the University of Wisconsin solution. Examples of further embodiments of suitable preservation solutions that may be combined with the compositions of the present invention to rejuvenate the small bowels comprise the Euro-Collins and the University of Wisconsin solutions.

The thiazolium compounds of formula (I) in the present invention can be prepared generally according to the methods described in Potts et al., 1976, J. Org. Chem. 41:187, and Potts et al., 1977, J. Org. Chem. 42:1648, or as shown in the following scheme wherein $R^1$, $R^2$, $R^3$, $R^4$, and X are as defined hereinabove for formula (I):

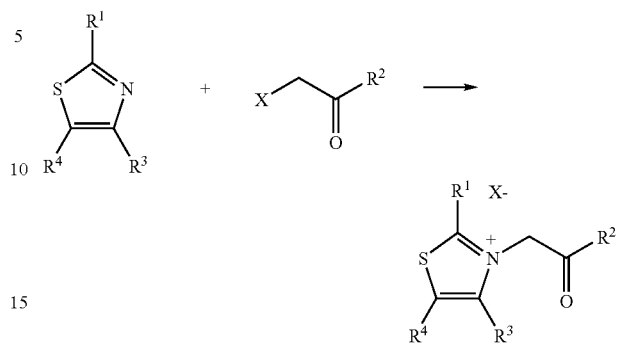

In the reaction scheme above, the appropriate substituted thiazole compounds of formula I is reacted with the appropriate halo compound to afford the desired compound of the present invention. The thiazole precursors wherein $R^1$ is —$CH(R^5)$—OH as defined hereinabove may be prepared as described in Noyce and Fike, J. Org. Chem. 1973;38: 3316–8, 3318–21, 3321–4, or as shown in the following scheme, wherein all substituents are as defined for formula (I) hereinabove.

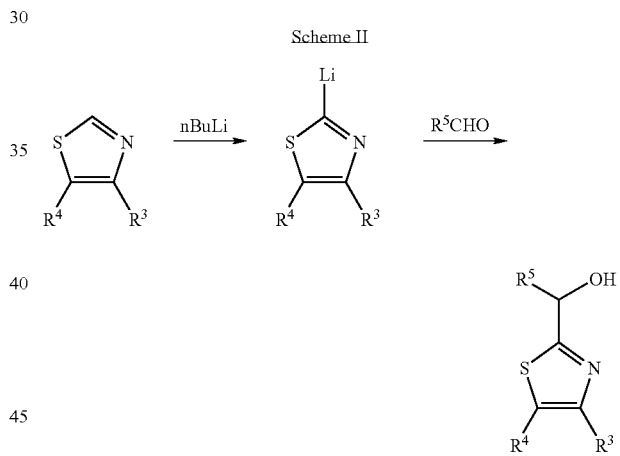

Compounds of formula (I) wherein $R^1$ is —$CH(R^5)$—OC(=O)—$R^6$ as defined hereinabove may be formed by acylation of the hydroxy group of the product of the above scheme by ester formation conditions known to those skilled in the art.

The halo reactant in Scheme 1, if not commercially available, may be prepared by suitable techniques known in the art. For example, for the preparation of 2-(1-hydroxyethyl)-3-[2-(1-pyrrolidinyl)-2-oxoethyl]thiazolium chloride, the reactant 1-(chloroacetyl)pyrrolidine may be prepared by dropwise addition of two equivalents of pyrrolidine in dichloromethane to 1 equivalent of chloroacetyl chloride in dichloromethane at 0 C.

The conditions for the reaction between the halo compound and the thiazole derivative most commonly involve heating the mixture at 70–110 C in an oil bath for 3–7 hours without solvent or with a minimum amount of solvent such as acetonitrile, or refluxing the mixture in ethanol or acetonitrile for 3–5 hours. If the halo reactant contains chlorine, the first condition is more often used. For a bromo compound, the second condition is usually preferable.

The naphthothiazole compounds of formula (II) are generally prepared by the methods described in Ulrich and Cerami, J. Med. Chem. 1982;25:654–657, and Lau and Gompf, J. Org. Chem. 1970;35:4103–4108, in which a suitably substituted thiourea derivative and a suitable 1,4-napthoquinone derivative are reacted in ethanolic HCl at room temperature or with heating for 14 days.

The pyridinium and pyrimidinium compounds of formula (III) can be prepared as described in Bansal et al., Chem. Ber. 1991;124:475–480, or by contacting an appropriate pyridine or pyrimidine precursor with a suitable halo derivative under conditions similar to those described for the reaction of thiazoles with halo derivatives in Scheme I hereinabove.

The 1-aminopyrimidinium derivatives of formula (IV) may be prepared as described in Tamura et al., J. Heterocycl. Chem. 1975;12:107–1 10, or by treating the pyridine or pyrimidine with O-mesitylenesulfonylhydroxylamine in a suitable solvent such as dichloromethane at ca. 0 C for several hours.

The imidazolium derivatives of formula (V) may be prepared as described in Porretta et al., Eur. J. Med. Chem. Chim. Ther. 1993;28:749–760, or in a two step procedure, in which a suitable halo derivative is reacted with imidazole followed by treatment with base to yield a 1-alkylated imidazole, which is then reacted with a second mole of a suitable halo derivative, giving a 1,3-dialkylimidazolium halide salt. This two-step procedure allows synthesis of symmetrical or unsymmetrical 1,3-dialkylimidazolium halides. Alternatively, symmetrical 1,3-dialkylimidazolium halides may be prepared in one step by reacting two equivalents of a suitable halo derivative with imidazole in the presence of magnesium carbonate or other insoluble base. Satisfactory solvents for these reactions include dichloromethane and acetonitrile, at temperatures of 25–110 C for several hours.

The halo reactant for synthesis of imidazolium derivatives of formula (V), if not commercially available, may be prepared by suitable techniques known in the art. For example, for the preparation of 1,3-bis[2-oxo-2-(2-thienyl)ethyl]imidazolium bromide, the reactant 2-(bromoacetyl)thiophene may be prepared according to the method of King et al., J. Org. Chem. 1964;29:3459, by the bromination of 2-acetylthiophene with copper (II) bromide.

Specific methods for the synthesis of compounds of formula (I), (II), (III), (IV), or (V) are described in the examples below.

The present invention may be better understood by reference to the following non-limiting examples, which are provided as exemplary of the invention. The following examples are presented in order to more fully illustrate embodiments of the invention. They should in no way be construed, however, as limiting the broad scope of the invention. All parts, percentage and proportions referred to herein and in the appended claims are by weight unless otherwise indicated.

EXAMPLE 1

Assay of Uncoupling Activity on Non-Enzymattically Browned BSA Coupled to Collagen Coated Plates Equipment, Reagents, and Other Materials
ELISA plate washer, Bio-Tek E1x-50
ELISA plate reader, Bio-Tek E1x-800
Incubator:
Collagen Type-I coated 96-well plates, Becton Dickson (Cat. #356407)
"Superblock" blocking solution, Pierce, Inc. (Cat. #37515)
10×PBS: purchased from Cellgro (Cat. #20–031) (Each liter contains 8 g NaCl, 2 g KCl,
2 g $KH_2PO_4$, and 11.50 g $Na_2HPO_4$)
1×PBS: diluted from above 10×PBS by distilled water, adjust to pH 7.4
PBS-Tween washing buffer: add Tween-20 (either 0.05% or 0.2%) to 1×PBS
Bovine Serum Albumin (BSA) (Type V), Sigma
Glucose, EM Science Non-Enzymatically Browned BSA:
Mix equal volume of BSA (50 mg/ml in 1×PBS) and glucose (0.5 M in PBS); keep the solution (after filtered through a 0.22 m filter and placed in a capped bottle) in a 37° C. incubator for 5 weeks.

Remove an aliquot of the solution and dialyze against 500-fold volume of PBS, with 4 changes of buffer within 2 days. Collect the solution, as AGE-BSA, from dialysis bag and determine the protein concentration. Aliquot and store at −20° C.

Anti-BSA antibody (rabbit IgG, conjugated with HRP), ICN (Cat. #55285)
TMB substrate solution, Pierce, Inc. (Cat. #34021)
2 M $H_2SO_4$ Procedure:
Add 300 1 of "Superblock" blocking solution to each well in a collagen Type-I coated 96-well plate; incubate at room temperature (RT) for 1 h.

During this hour,
Rinse the plate washer with autoclaved $dH_2O$ and then flush 3 times with PBS-Tween washing buffer containing 0.05% of Tween-20.
Dilute AGE-BSA in 1×PBS to 0.03 g/l. Confirm protein concentration by Bradford assay.
After 1 h-blocking of the plates, wash 3 times with above wash buffer.
In triplicate, add 50 1 of PBS into the blank wells and 50 1 of diluted AGE-BSA (~1.5 g) to other wells (according to the experimental arrangement).
Incubate the plate in a 37° C. incubator for 4 h.
Wash 8 times with PBS-0.05% Tween washing buffer in two directions, 4 times/direction.
Prepare solutions of test compounds in 1×PBS (or in $H_2O$) at desired concentrations.
Add 50 1 of PBS or test compounds in PBS to appropriate wells.
Place the plate in a box with wet paper tower, incubate in a 37° C. incubator for the desired test time. (Record the hours of incubation.)
In the meantime, run maintenance program (Overnight rinse/soak) on the plate washer using autoclaved distilled $H_2O$.
After incubation, flush the plate washer 3 times with PBS-Tween washing buffer.
Wash the plate 4 times with 1×PBS buffers containing 0.2% Tween-20.
Wash 6 more times with PBS-0.05% Tween washing buffer in two directions, 3 times/direction.
Prepare 1:8000 dilution (in 1×PBS) of anti-BSA antibody (rabbit IgG-HRP)
Add 50 1 of diluted antibody to the wells, incubate at room temperature for 30 min.

Wash 8 times with PBS-0.05% Tween washing buffer in two directions, 4 times/direction.

Add 100 1 of TMB substrate solution to the wells; incubate at RT for 15 min.

Stop the reaction by adding 100 1 of 2 M $H_2SO_4$.

Read absorbance at 450 nm in an ELISA plate reader.

Plot and analyze data. The % AGE-uncoupling activity of each test compound is calculated according to the formula:

(1-(NON-ENZYMATICALLY BROWNED-BSA bound after test compound/NON-ENZYMATICALLY BROWNED-BSA bound without test compound))×100%

The above-detailed test method is hereinafter identified as "Assay of Uncoupling Activity." The results of testing the compounds for uncoupling sugar-mediated coupling are summarized in Tables 3 and 4.

TABLE 3

Uncoupling of sugar-mediated coupling of albumen to collagen by test compounds.

| Compound | % uncoupling at 10 mM, 2 days | % uncoupling at 20 mM, 1 day |
|---|---|---|
| 4,5-Dimethyl-3-(2-oxo-2-phenylethyl)-thiazolium chloride | 52 | 39 |
| 2,3-Diaminopyrimidinium mesitylene-2-sulfonate | 38 | |
| 3-(2-Oxo-2-phenylethyl)-2-(1-hydroxyethyl)-thiazolium bromide | 54 | |
| 3-(2-Oxo-2-phenylethyl)-2-(1-benzoyloxyethyl)thiazolium bromide | | 68 |
| 2-(1-hydroxyethyl)-3-[2-oxo-2-(1-pyrrolidinyl)ethyl]thiazolium chloride | 32 | |
| 2,4-Dimethyl-3-(2-oxo-2-phenylethyl)-thiazolium bromide | 36 | 51 |
| 2-Ethyl-4-methyl-3-(2-oxo-2-phenylethyl)-thiazolium bromide | | 57 |
| 2-benzyl-1-(2-oxo-2-phenylethyl)pyridinium bromide | | 54 |
| 3-carboxymethyl-2-(1-hydroxyethyl)thiazole | | 47 |
| 5,6-Dihydro-8-methyl-6-oxo-8H-thiazolo-[2,3-c](1,4)oxazin-4-ium bromide | | 36[a] |
| 1-[2-(1-pyrrolidinyl)-2-oxoethyl]-2-(cyanomethyl)pyridinium bromide | 68 | |
| 3-[2-Oxo-2-phenylethyl]-2-(1-acetoxyethyl)-thiazolium bromide | | 52 |
| 3-[2-Oxo-2-(1-pyrrolidinyl)ethyl]-2-(1-acetoxyethyl)thiazolium bromide | | 46 |
| 2-Methyl-3-(2-oxo-2-phenylethyl)-7-oxo-5,6,7,8-tetrahydropyrimidino[4,5-d]pyrimidin-3-ium bromide | | 22[a] |
| 1,3-bis(2-oxo-2-phenylethyl)imidazolium bromide | | 25[b] |
| 4,5-dimethyl-2-(1-hydroxyethyl)-3-(2-oxo-2-phenylethyl)thiazolium bromide | | 45 |
| 2,3,8-Trimethyl-6-phenyl-8H-thiazolo[2,3-c](1,4)oxazin-4-ium bromide | | 34 |

[a] at 30 mM,
[b] at 10 mM

TABLE 4

Uncoupling of sugar-mediated coupling of albumen to collagen by naphthothiazolium test compounds.

| Compound | % uncoupling at 5 mM, 1 day |
|---|---|
| 1-ethyl-2-(ethylimino)-1,2-dihydro-4-methylnaphtho[1,2-d]thiazol-5-ol monohydrochloride | 59 |

TABLE 4-continued

Uncoupling of sugar-mediated coupling of albumen to collagen by naphthothiazolium test compounds.

| Compound | % uncoupling at 5 mM, 1 day |
|---|---|
| 1-ethyl-2-(ethylimino)-1,2-dihydro-4-methylnaphtho[1,2-d]thiazol-5-ol monohydrochloride | 58 |
| 4-methyl-2-[[3-(4-morpholino)propyl]amino]-naphtho[1,2-d]thiazol-5-ol dihydrochloride | 36 |
| 2-(Cyclohexylimino)-1,2-dihydro-4-methyl-1-[3-(4-morpholino)propyl]naphtho[1,2-d]thiazol-5-ol dihydrochloride | 22 |
| 2-(Cyclohexylimino)-1,2-dihydro-4-methyl-1-[3-(4-methyl-1-piperazinyl)propyl]naphtho[1,2-d]-thiazol-5-ol trihydrochloride | 21 |
| 1,2-dihydro-1-[3-(dimethylamino)propyl]-4-methyl-2-[(1-methylethyl)imino]naphtho[1,2-d]thiazol-5-ol dihydrochloride | 19 |

EXAMPLE 2

2,3-Diaminopyrimidinium mesitylene-2-sulfonate

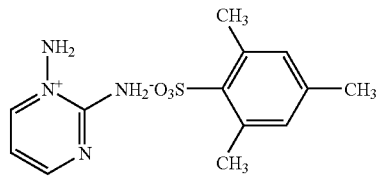

2-Aminopyrimidine (0.8 g, 8.41 mmole) in dichloromethane (16 mL) at 4 C was treated dropwise with O-mesitylenesulfonylhydroxylamine (2.65 g, 12.3 mmole) in dichloromethane (10 mL). After stirring overnight at 4 C, ether (25 mL) was added and the mixture stored at 4 C for 3 hr. The product was filtered out and washed with 1:1 dichloromethane/ether, (50 mL) giving 2.26 g crude product. Recrystalization from methanol/dichloromethane/ether gave 2.12 g of the title compound, mp 190–191 C. Ref.: Tamura et al., J. Heterocycl. Chem. 1975;12:107.

EXAMPLE 2a

1-Amino-2,4,6-trimethylpyrimidinium mesitylene-2-sulfonate

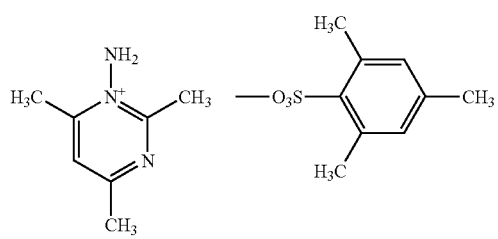

2,4,6-trimethylpyrimidine dihydrate (0.79 g, 5.0 mmole, prepared from acetylacetone and acetamidine hydrochloride according to A. Bowman, J. Chem. Soc. 1937;494–495) in dichloromethane (10 mL) was dried over Na$_2$SO$_4$ and filtered. Separately, O-(mesitylenesulfonyl)hydroxylamine containing ca. 25% water (1.57 g, ca. 5.4 mmole) was dissolved in dichloromethane (10 mL) and dried over Na$_2$SO$_4$ and filtered. The dry O-(mesitylenesulfonyl)hydroxylamine filtrate was added dropwise to the dry 2,4,6-trimethylpyrimidine filtrate at 0 C. Stirring was continued 5 hr at 0 C and then 16 hr at 4 C. The reaction mixture was concentrated at reduced pressure to ca. 10 mL and treated with ca. 3 mL ether to cause separation of a white powder, which was filtered, washed with 10 mL 1:1 dichloromethane/ether, and dried to yield 1.27 of crude product in two crops. Recrystallization from methanol/dichloromethane/ether gave 1.18 g of the title compound, mp 183–185 C.

EXAMPLE 2b 1,2-Diamino-4,6-dimethylpyrimidinium mesitylene-2-sulfonate

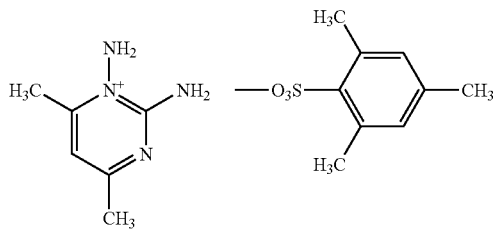

O-(Mesitylenesulfonyl)hydroxylamine containing ca. 18% water (3.03 g, 2.56 g dry wt., ca. 11.9 mmole) was dissolved in dichloromethane (15 mL) and dried over Na$_2$SO$_4$ and filtered. This was added dropwise to a solution of 2-amino-4,6-dimethylpyrimidine (1 g, 8.12 mmole) in 1:6 methanol-dichloromethane (10.5 mL) in an ice bath with stirring. Stirring was continued at 4 C overnight. Ether (20 mL) was added and the mixture was stirred at 4 C for 3 hr. The crude product was filtered out and dried (2.50 g). This was dissolved in a minimum amount of methanol, filtered and reduced in volume to 10 mL under reduced pressure. The solution was diluted with dichloromethane (15 mL) and then with ether (15 mL). After stirring at room temp. for 2 hr, the title compound was collected as crystal flakes and dried (2.26 g, mp 242–243 C).

EXAMPLE 2c 1,2-diamino-4-methylpyrimidinium mesitylene-2-sulfonate

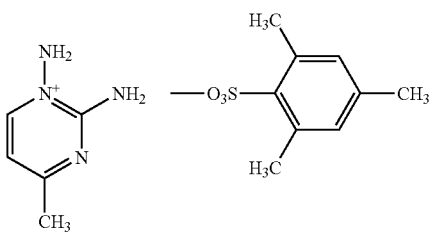

and 1,2-diamino-6-methylpyrimidinium mesitylene-2-sulfonate.

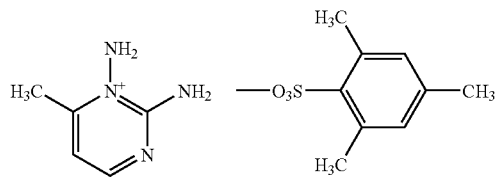

O-(Mesitylenesulfonyl)hydroxylamine containing ca. 18% water (3.5 g, 2.88 g dry wt., ca. 13.4 mmole) was dissolved in dichloromethane (18 mL) and dried over Na$_2$SO$_4$ and filtered. This was added dropwise to a solution of 2-amino-4-methylpyrimidine (1 g, 9.14 mmole) in 3:4 methanol-dichloromethane (14 mL) in an ice bath with stirring. Stirring was continued at 4 C overnight. Ether (30 mL) was added and the mixture was stirred at 4 C for 4 hr. Filtration and drying afforded a mixture of the crude aminated product. (2.4 g). This was dissolved in methanol and filtered, and concentrated under reduced pressure to 15–20 mL. Ether (20 mL) was added, and the mixture was stirred at room temp. for 2 hr. Filtration, washing with 1:1 dichloromethane-ether and drying gave 0.92 g of a fraction, mp 209–212 C, consisting mainly of 1,2-diamino-6(or 4)-methylpyrimidinium mesitylene-2-sulfonate. Storage of the filtrate overnight resulted in deposition of more crystals, which were filtered out and washed with 1:1 dichloromethane-ether to give 1.06 g of a fraction, mp 166–168 C, consisting mainly of 1,2-diamino-4(or 6)-methylpyrimidinium mesitylene-2-sulfonate. Isomer assignment is tentative.

EXAMPLE 2d 1,4-diamino-2,6-dimethylpyrimidinium mesitylene-2-sulfonate

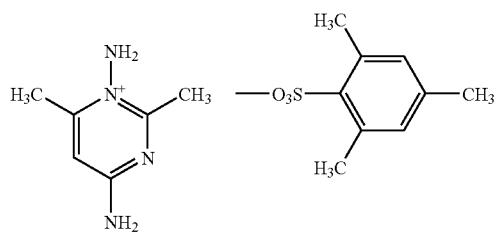

and 1,6-diamino-2,4-dimethylpyrimidinium mesitylene-2-sulfonate.

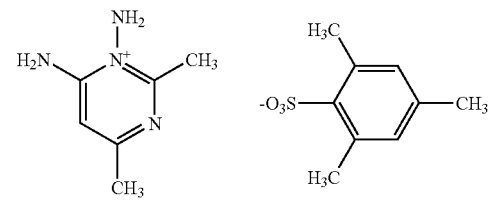

O-(Mesitylenesulfonyl)hydroxylamine containing ca. 18% water (3.03 g, 2.56 g dry wt., ca. 11.9 mmole) was dissolved in dichloromethane (15 mL) and dried over Na$_2$SO$_4$ and filtered. This was added dropwise to a solution of 4-amino-2,6-dimethylpyrimidine (1 g, 8.12 mmole) in 1:6 methanol-dichloromethane (10.5 mL) in an ice bath with stirring for 2 hr. Ether (20 mL) was added and the mixture was stored at 4 C for 18 hr. The crude aminated product was filtered out and dried (2.65 g). This was dissolved in a minimum amount of methanol, filtered and reduced in volume to ca. 20 mL under reduced pressure. This was diluted with dichloromethane (15 mL) and ether (20 mL) was added, and the mixture was stirred at room temp. for 2 hr. Filtration, washing with 1:1 dichloromethane-ether and drying gave 0.73 g of a fraction, mp 262–264 C, consisting mainly of 1,6(or 4)-diamino-2,4(or 6)-dimethylpyrimidinium mesitylene-2-sulfonate. Storage of the filtrate resulted in deposition of more crystals, which were filtered out and washed with 1:1 dichloromethane-ether to give 1.39 g in two crops of a fraction, mp 194–196 C, consisting mainly of 1,4(or 6)-diamino-2,6(or 4)-dimethylpyrimidinium mesitylene-2-sulfonate. Isomer assignment is tentative.

EXAMPLE 3

3-(2-Oxo-2-phenylethyl)-2-(1-hydroxyethyl)thiazolium bromide

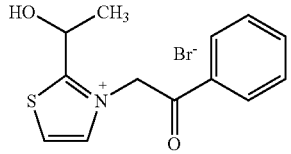

1-(2-Thiazolyl)ethanol (0.71 g, 5.49 mmole), 2-bromo-1-phenyl-1-ethanone (1.09 g, 5.47 mmole), and acetonitrile (0.6 mL) were combined and heated with stirring at 130 C for 4 hr. After cooling, water (20 mL) was added and the mixture was filtered and extracted twice with ether. The aqueous layer was treated with active carbon and filtered to give a clear solution which was concentrated in vacuo to 1.52 g of residue, which was crystallized from acetonitrile/ether and recrystallized twice from methanol/acetonitrile/ether to give 0.77 g of the title compound as prisms, mp 157–158 C; calc'd for C$_{13}$H$_4$NO$_2$SBr: C, 47.55; H, 4.33; N, 4.26; found: C, 47.52; H, 4.32; N, 4.14.

EXAMPLE 4

3-(2-Oxo-2-phenylethyl)-2-(1-benzoyloxyethyl)thiazolium bromide

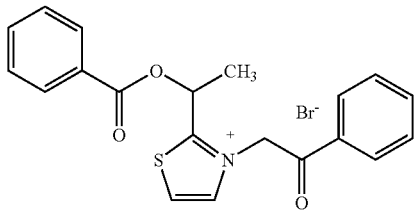

1-(2-Thiazolyl)ethyl benzoate (2.0 g, 8.5 mmole), 2-bromo-1-phenyl-1-ethanone (1.7 g, 8.5 mmole), and acetonitrile (0.4 mL) were combined and heated at 115 C with stirring for 3 hr. After cooling, the reaction was diluted with 50 mL dichloromethane and extracted with 5×30 mL water. The combined, filtered water layers were evaporated to yield 2.2 g crude product, which crystallized from acetonitrile/ether after several days to afford 1.22 g of the title compound, mp 130–131.5 C.

EXAMPLE 5

2-(1-hydroxyethyl)-3-[2-oxo-2-(1-pyrrolidinyl)ethyl]thiazolium chloride

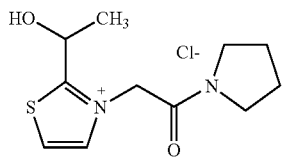

1-(2-Thiazolyl)ethanol (1.14 g, 8.8 mmole), N-chloroacetylpyrrolidine (1.30 g, 8.8 mmole), and acetonitrile (1.25 mL) were combined and heated at reflux in an oil bath at 105–110 C for 6 hr. Acetonitrile (8 mL) was added and heating was continued 10 min. The cooled, clear solution was treated with ether (10 mL), causing an oil to separate, which crystallized on standing at room temp. overnight. Filtration and washing with 30% ether/acetonitrile gave 1.86 g crude product which was dissolved in methanol, decolorized, and evaporated to dryness. The residue was recrystalized from acetonitrile/ether and from methanol/acetonitrile/ether to yield 1.63 g of the title compound, mp 189–190 C (dec.).

EXAMPLE 5a

3-Amino-2-(1-hydroxyethyl)thiazolium mesitylene-2-sulfonate

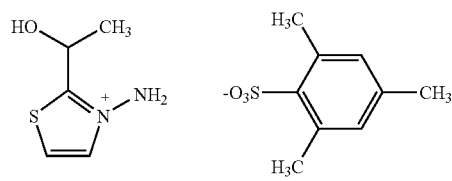

O-(Mesitylenesulfonyl)hydroxylamine containing ca. 18% water (1.95 g, 1.60 g dry wt., ca. 7.4 mmole) was dissolved in dichloromethane (12 mL) and dried over Na$_2$SO$_4$ and filtered. This was added dropwise to a solution of 1-(2-thiazolyl)ethanol (0.8 g, 6.2 mmole) in dichloromethane (4 mL) at 0 C. After stirring an additional 12 hr at 4 C, the mixture was diluted with ether (13 mL) and stored at 4 C for 1 hr. The supernatant was decanted from the syrupy precipitate, which was triturated with 1:1 dichloromethane-ether (10 mL) to yield a powder which was filtered out, washed with the same solvent, and dried to yield 1.71 g of the title compound, mp 105–107 C.

EXAMPLE 6

2,4-Dimethyl-3-(2-oxo-2-phenylethyl)thiazolium bromide

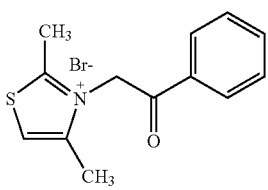

2,4-Dimethylthiazole (0.5 g, 4.41 mmole), 2-bromo-1-phenyl-1-ethanone (0.879 g, 4.41 mmole), and acetonitrile (0.25 mL) were heated in an oil bath at 105 C for 1.5 hr. Product precipitation began within 10 min. After cooling, acetonitrile (5 mL) and ether (4 mL) were added and the mixture stood at room temp. overnight. Filtration and washing with 30% ether/acetonitrile gave 1.2 g crude product which was recrystalized from methanol/acetonitrile/ether to afford 0.97 g of the title compound, mp 235–237 C (dec.).

EXAMPLE 7

2-Ethyl-4-methyl-3-(2-oxo-2-phenylethyl)thiazolium bromide

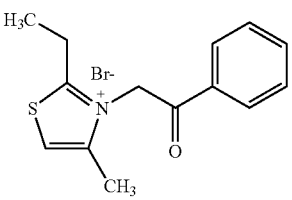

2-Ethyl-4-methylthiazole (0.5 g, 3.93 mmole), 2-bromo-1-phenyl-1-ethanone (0.782 g, 3.93 mmole), and acetonitrile (0.25 mL) were heated in an oil bath at 110 C for 3 hr, then cooled, dissolved in acetonitrile (4 mL), and diluted with ether (4 mL). After storage at 4 C overnight, the crystals which separated were filtered out and recrystalized from acetonitrile/ether to give 0.765 g of the title compound, mp 126–128.

EXAMPLE 8

2-benzyl-1-(2-oxo-2-phenylethyl)pyridinium bromide

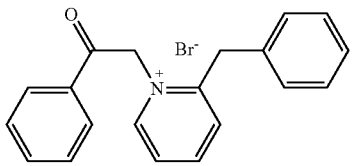

Prepared by reacting 2-benzylpyridine with 2-bromo-1-phenyl-1-ethanone according to known procedures:
Moser and Bradsher, J. Amer. Chem. Soc. 1959;81:2547; Kroehnke et al., Justus Liebigs Ann. Chem., 1964;679: 136; Bansal, Raj K.; Karaghiosoff, Konstantin; Gupta, Neelima; Schmidpeter, Alfred; Spindler, Claudia, Chem. Ber. 1991;124:475–480; Schliemann, W.; Buege, A., Pharmazie, 1980;35:203–204.

EXAMPLE 9

3-carboxymethyl-2-(1-hydroxyethyl)thiazole

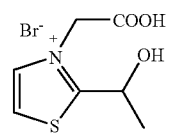

1-(2-Thiazolyl)ethanol (0.5 g, 3.87 mmole) and bromoacetic acid (0.538 g, 3.87 mmole) were warmed to melt the bromoacetic acid, then were allowed to cool and were stirred 4 days at room temp. The mixture was dissolved in 15–20 mL water and extracted with 4×10 mL ether. The water layer was evaporated in vacuo to give 0.79 g of residue, which was stored under 30 mL acetonitrile at room temp. overnight to effect crystalization. Filtration and washing with 30% ether/acetonitrile gave 0.335 g of the title compound, mp 160–161 C.

EXAMPLE 9a

1-(2-ethoxy-2-oxoethyl)-2-(1-hydroxyethyl)thiazolium bromide

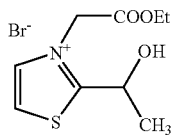

A mixture of 1-(2-thiazolyl)ethanol (1.17 g, 8.67 mmole) and ethyl bromoacetate (1.32 g, 8.63 mmole) was heated at 48 C for 18 hr. The reaction mixture was dissolved in acetonitrile (3 mL) and stored at 4 C. After 2 months the crystals which separated were filtered out and washed with 3:7 ether-acetonitrile to yield 2.028 g of the title compound, mp 101–103 C.

EXAMPLE 10

5,6-Dihydro-8-methyl-6-oxo-8H-thiazolo[2,3-c](1,4)oxazin-4-ium bromide

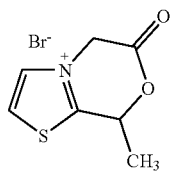

1-(2-Thiazolyl)ethanol (0.5 g, 3.87 mmole), bromoacetic acid (0.537 g, 3.86 mmole), and acetonitrile (0.125 mL) were heated in an oil bath with stirring at 105 C for 6 hr. The mixture was dissolved in 5 mL 4:1 acetonitrile/methanol and stored at 4 C for 17 hr. The crystals which separated were filtered out and combined from two identical runs, and recrystalized from methanol/acetonitrile/ether to give a total of 0.32 g of the title compound, mp 214–215.5 C. Calcd for $C_7H_8NO_2SBr$: C, 33.5; H, 3.20; N, 5.59; found: C, 33.62; H, 3.16; N, 5.61.

EXAMPLE 11

1-[2-(1-pyrrolidinyl)-2-oxoethyl]-2-(cyanomethyl)pyridinium bromide

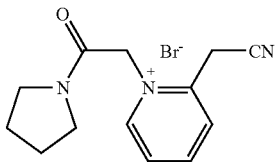

2-Pyridineacetonitrile (0.8 g, 6.77 mmole) and 1-(bromoacetyl)pyrrolidine (1.3 g, 6.77 mmole) were warmed to melt the 1-(bromoacetyl)pyrrolidine, then stirred at room temp. for 3 days. The mixture was dissolved in acetonitrile (5 mL) and ether (2 mL) and stored at 4 C for 3 days. The crystals which separated were filtered out to yield a crude product which was dissolved in methanol, decolorized, evaporated, and the residue triturated with 30% ether-acetonitrile to obtain 0.72 g of the title compound, mp 150–152 C.

EXAMPLE 12

1-[2-(1-pyrrolidinyl)-2-oxoethyl]-2-(cyanomethyl)pyridinium chloride

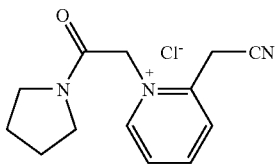

1-[2-(1-Pyrrolidinyl)-2-oxoethyl]-2-(cyanomethyl)pyridinium bromide (0.74 g, 2.39 mmole) was dissolved in water (3 mL), loaded onto an Amberlite IRA-400 column (chloride form, 2.5 cm×19 cm) and eluted with distilled water. Fractions 1 (30 mL) and 2 (20 mL) were evaporated under reduced pressure and the residue was recrystalized from acetonitrile-ether to give the title compound as 0.512 g of prisms, mp 130–132° C. Calcd for $C_{13}H_{16}N_3OCl$: C 58.70, H 6.02, N 15.80, Cl 13.34; found: C, 58.68; H, 6.24; N, 15.88, Cl 13.31.3-(2-Oxo-2-phenylethyl)-2-(1-acetoxyethyl)thiazolium bromide.

EXAMPLE 13

3-[2-Oxo-2-phenylethyl]-2-(1-acetoxyethyl)thiazolium bromide

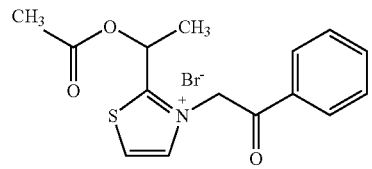

1-(2-Thiazolyl)ethyl acetate (0.8 g, 4.67 mmole) and 2-bromo-1-phenyl-1-ethanone (0.93 g, 4.67 mmole) were combined and stirred at room temp. for 5 days. The viscous mixture was dissolved in acetonitrile (5 mL), diluted with ether (3 mL), and stored overnight at 4 C. The resulting crystals (1.5 g) were recrystallized from acetonitrile/ether to afford 0.97 g of the title compound, mp 155–156 C.

EXAMPLE 14

3-[2-Oxo-2-(1-pyrrolidinyl)ethyl]-2-(1-acetoxyethyl)thiazolium bromide

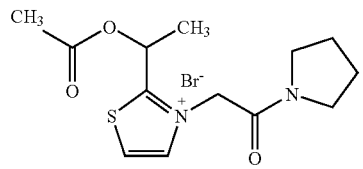

In a manner analogous to the preceding, using 1-(bromoacetyl)pyrrolidine (0.897 g, 4.67 mmole) in place of 2-bromo-1-phenyl-1-ethanone, the title compound was prepared in the amount of 0.74 g, mp 70–72 C.

EXAMPLE 15

2-Methyl-3-(2-oxo-2-phenylethyl)-7-oxo-5,6,7,8-tetrahydropyrimidino [4,5-d]pyrimidin-3-ium bromide

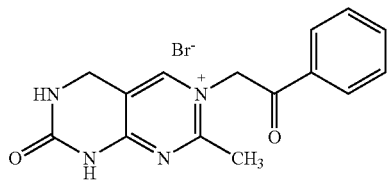

2-Methyl-7-oxo-5,6,7,8-tetrahydropyrimidino[4,5-d]pyrimidine (0.1 g, 0.6 mmole) and 2-bromo-1-phenyl-1-ethanone (0.12 g, 0.6 mmole) in ethanol (20 mL) were heated at reflux for 32 hr. After cooling, the precipitated hydrobromide (mp>310 C) of the starting heterocycle was filtered out, and the filtrate was diluted with ether to form a precipitate which was recrystalized from methanol-ether to yield 47.5 mg of the title compound, mp 249–250 C.

EXAMPLE 15a 1-(2-oxo-2-phenylethyl)-2,4,6-trimethylpyrimidinium bromide

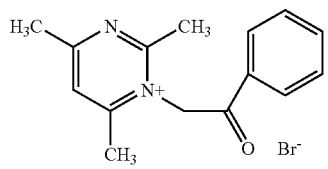

Analogously to the preceding example, one skilled in the art may treat 2,4,6-trimethylpyrimidine with an equivalent amount of 2-bromo-1-phenyl-1-ethanone, neat or with a minimal amount of solvent such as acetonitrile, at ambient or elevated temperature for 1 or more days to produce the title compound after dilution with suitable solvent such as acetonitrile or ether and filtration.

EXAMPLE 16

1,3-bis(2-oxo-2-phenylethyl)imidazolium bromide

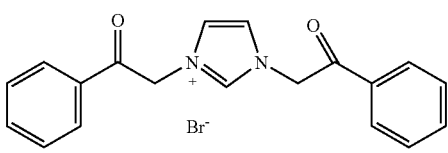

Imidazole (0.5 g, 7.34 mmole) was dissolved in acetonitrile (2 mL) and treated with 2-bromo-1-phenyl-1-ethanone (2.93 g, 14.72 mmole) and magnesium carbonate (0.31 g, 3.67 mmole) with stirring at 110 C (oil bath temp.) for 4.5 hr. After cooling and standing overnight at room temp., the mixture was diluted with 20% ether/methanol to give 2.25 g of crude product which was recrystalized from methanol-ether to give 1.54 g of the title compound, mp 260–262° C.

EXAMPLE 16a 1,3-Bis[2-oxo-2-(1-pyrrolidinyl)ethyl]imidazolium chloride

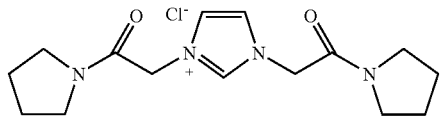

Imidazole (0.5 g, 7.34 mmole) was dissolved in acetonitrile (0.75 mL) and treated N-(chloroacetyl)pyrrolidine (2.16 g, 14.63 mmole) and magnesium carbonate (0.31 g, 3.67 mmole). The mixture was heated at 100 C for 4 hr, and then at 70 C for two days. Acetonitrile was added and the mixture was stirred, and filtered, and the precipitate was washed with acetonitrile. This was repurified by dissolution in ethanol and precipitation with acetonitrile to give 1.42 g of the title compound as an amorphous, hygroscopic powder.

EXAMPLE 17

4,5-dimethyl-2-(1-hydroxyethyl)-3-(2-oxo-2-phenylethyl)thiazolium bromide

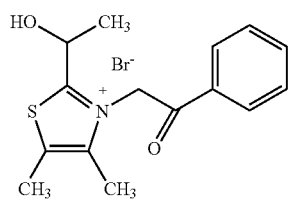

1-(4,5-dimethyl-2-thiazolyl)ethanol (0.24 g, 1.5 mmole), 2-bromo-1-phenyl-1-ethanone (0.3 g, 1.5 mmole) and acetonitrile (0.1 mL) were heated at 45° C. with stirring for 1 hr, then stored at 37° C. for 20 hr, and at 25° C. for 26 hr. The partially solidified mixture was washed with ether and acetonitrile-ether to give 0.25 g of crude product which was recrystalized from acetonitrile-ether to give 0.18 g of the title compound, mp 174–176° C. Calcd for $C_{15}H_{18}NO_2SBr$: C, 50.57; H, 5.09; N 3.93. Found, C, 50.37; H, 5.09; N, 3.88.

EXAMPLE 18

2,3,8-Trimethyl-6-phenyl-8H-thiazolo[2,3-c](1,4)oxazin-4-ium bromide

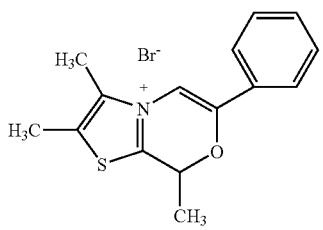

1-(4,5-Dimethyl-2-thiazolyl)ethyl acetate (1.28 g, 6.4 mmole), 2-bromo-1-phenyl-1-ethanone (1.28 g, 6.4 mmole), and acetonitrile (0.5 mL) were heated at 105 C with stirring for 3.5 hr. The mixture was diluted with water (60 mL), filtered with water washes (20 mL), and the filtrate was extracted with ether (30 mL). The aqueous phase was evaporated to dryness in vacuo yielding 1.8 g crude product, which was dissolved in acetonitrile, diluted with ether, and stored at room temp. for several days to produce needle-like crystals which were recrystallized from methanol/acetonitrile/ether to give 0.57 g of the title compound, mp 236 C (dec.).

EXAMPLE 19

1-[2-(1-pyrrolidinyl)-2-oxoethyl]-2-benzylpyridinium bromide

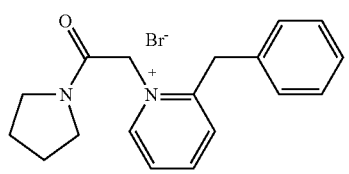

2-Benzylpyridine (1.0 g, 5.9 mmole) and 1-(bromoacetyl)pyrrolidine (1.134 g, 5.9 mmole) were heated with stirring in an oil bath at 98° C. for 2 hr. The viscous mixture was dissolved in 10 mL 4:1 acetonitrile-methanol and stored at 4° C. for 2 days. The crystals which separated were filtered out to give 1.96 g of crude product which was recrystalized from methanol-acetonitrile to give 1.45 g of the title compound, mp 224–226° C.

EXAMPLE 20

2-(Cyclohexylimino)-1,2-dihydro-4-methyl-1-[3-(dimethylamino)-propyl]-naphtho[1,2-d]thiazol-5-ol dihydrochloride

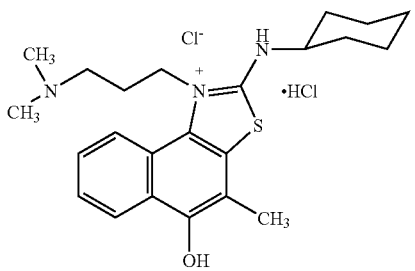

A solution of cyclohexyl isothiocyanate (5.65 g, 40 mmole) (Aldrich Chemical, Milwaukee, Wis.) in diethyl ether (15 ml) was added to a stirred solution of 3-dimethylaminopropylamine (4.2 g, 41 mmole) (Aldrich) in isopropanol (15 ml) with cooling in an ice bath. The mixture was allowed to reach room temperature and was stirred for 16 hr. The crystalline N-cyclohexyl-N-(3-dimethylaminopropyl)thiourea which separated was filtered out and washed with ether, yielding 7.3 g (75%) white solid, melting pt. 62–67° C. A portion of this thiourea derivative (2.43 g, 10 mmole) was dissolved in ethanol (12.5 ml) containing aq. conc. HCl (1.75 ml, 20 mmole). To this stirred solution was added a hot solution of 2-methyl-1,4-naphthoquinone (3.44 g, 20 mmole) in ethanol (25 ml). The hot mixture was allowed to cool and was stored at room temperature in the dark for 2 days. The crude product which separated was filtered out and washed with ethyl acetate to yield 1.86 g of crude product. Of this, 1.5 g was recrystallized by dissolving in 20 ml hot ethanol and adding 120 ml of warm acetone; the white powder which separated on cooling was filtered out and washed with ethyl acetate to give 1.14 g (30%) of the title compound, melting pt. 250–255° C. (dec.).

EXAMPLE 21

2-[[3-[1-[2-(Aminoiminomethyl)hydrazono]ethyl]phenyl]amino]-4-methyl-naphtho[1,2-d]thiazol-5-ol

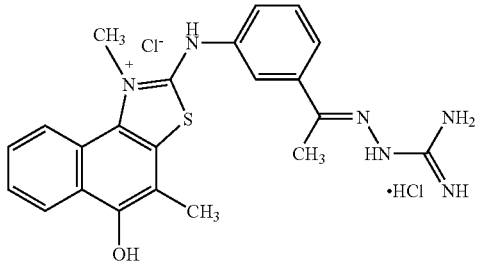

3-Acetylaniline (6.76 g, 50 mmole) in ethanol (50 mL) was treated with methyl isothiocyanate (3.42 mL, 50 mmole). After stirring 18 hr at room temperature, the crystalline N-(3-acetylphenyl)-N'-methylthiourea product was filtered out (7.75 g, 75% yield, mp 119–120° C.). This thiourea (3.5 g, 16.8 mmole) was combined with 2-methylnaphtboquinone (5.8 g, 33.6 mmole) in 35 mL ethanol in the presence of 12N aq. HCl (1.4 mL, 16.8 mmole). After 24 hr, filtration and washing with ethanol, ethyl acetate and ether and air drying gave 2-(3-acetylphenyl)amino-1,4-dimethyl-5-hydroxynaphtho[1,2-d]thiazolium chloride (1.62 g, 24%). This keto naphthothiazolium salt (0.80 g, 2.0 mmole) was heated at reflux in 80% methanol (12 mL) containing aminoguanidine hydrochloride (0.24 g, 2.2 mmole) for 40 hr and allowed to cool. Filtration 0.80 g off-white powder. Recrystallization of 0.75 g from methanol gave 0.42 g of the title compound as a pale yellow powder, mp 252–257° C. (dec.).

EXAMPLE 22

4-Methyl-2-[[3-(4-morpholino)propyl]amino]naphtho[1,2-d]thiazol-5-ol dihydrochloride

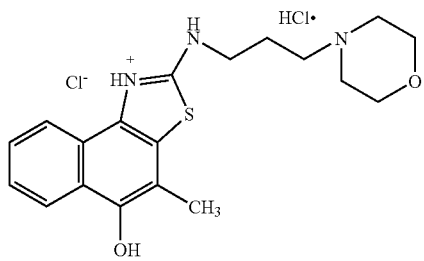

A solution of 1.016 g (5 mmole) 1-[3-(4-morpholino)propyl]thiourea (Trans World Chemicals, Rockville Md.) in 15 mL warm ethanol containing 0.83 mL conc. HCl (10 mmole) was added to a solution of 1.72 g (10 mmole) 2-methyl-1,4-naphthoquinone (Alfa Aesar/Avocado, Ward Hill Mass.) in 15 mL hot ethanol. The brown solution was allowed to stand for 6 days, then filtered and the solids washed with ethyl acetate and dried to give 1.479 g crude product. Recrystallization of 1 g from 50 mL methanol+100 mL ethyl acetate gave 0.883 g of the title compound, melting pt. 266–270° C. (dec.).

EXAMPLE 23

8-[1-[2-(Aminoiminomethyl)hydrazono]ethyl]-2-(butylimino)-1,2-dihydro-1,4-dimethylnaphtho[1,2-d]thiazol-5-ol

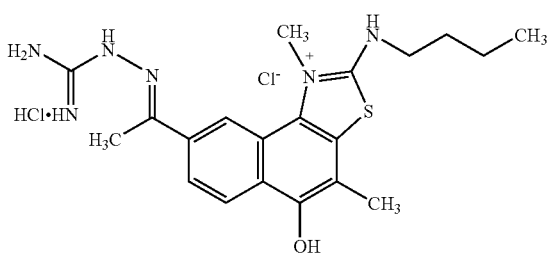

6'-Methyl-2'-acetonaphthone (Aldrich Chemical Co., 5.52 g, 30 mmole) in acetic acid (22 mL) was treated dropwise with a solution of chromium trioxide (15 g, 150 mmole) in aq. 45% (v/v) acetic acid (20 mL) with stirring and cooling in a 25 C water bath. After stirring 16 hr at room temp., the mixture was diluted with 200 mL water. The yellow solid which separated was filtered out and recrystallized from isopropanol (40 mL) to give 6-acetyl-2-methyl-1,4-naphthoquinone (2.82 g, 44%), mp 126 C. This quinone (1.284 g, 6.0 mmole) was combined with N-butyl-N'-methylthiourea (Kjaer and Rubinstein, 1953, Acta Chem. Scand. 7:528–536) (0.584 g, 4 mmole) in ethanol (20 mL), treated with 12N HCl (0.34 mL, 4 mmole), heated to reflux and allowed to cool. After 42 hr at room temp., filtration gave 8-acetyl-2-butylamino-1,4-dimethyl-5-hydroxynaphtho[1,2-d]thiazolium chloride (0.515 g, 34%). This keto thiazolium salt (0.284 g, 0.75 mmole) was heated at reflux with aminoguanidine HCl (0.110 g, 1 mmole) in aq. 85% ethanol (7 mL) for 44 hr. Cooling and filtration gave the title compound (0.170 g, 48%), mp 260–264 C (dec.).

EXAMPLE 24

2-(Cyclohexylimino)-1,2-dihydro-4-methyl-1-[3-(4-morpholino)propyl]naphtho[1,2-d]thiazol-5-ol dihydrochloride

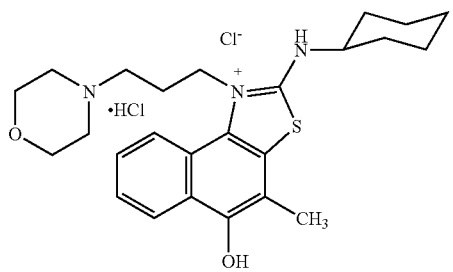

Cyclohexyl isothiocyanate (1.483 g, 10.5 mmole) was added to a solution of 3-(4-morpholino)propylamine (Aldrich) (1.514 g, 10.5 mmole) in t-butyl methyl ether (15 mL). After 16 hr at room temp., the solution was concentrated in vacuo and the residue was stored under 3 mL heptane at 4° C. for 24 hr to induce crystallization. The heptane was decanted and the crude solid was triturated with t-butyl methyl ether and filtered to give 1.94 g (65%) of 1-cyclohexyl-3[(4-morpholino)propyl]thiourea, melting pt.8587° C. This thiourea (1.427 g, 5 mmole), in 7.5 mL ethanol containing 0.83 mL (10 mmole) conc. HCl, was added to a solution of 1.722 g (10 mmole) 2-methyl-11,4-naphthoquinone in 15 mL warm 1:1 ethanol/ethyl acetate with stirring. After 15 days at room temp., dilution with t-butyl methyl ether gave 1.44 g of crude product after filtration. Of this, 1.0 g was recrystalized from 70 mL 1:3:10 methanol/ethanol/ethyl acetate to give 0.652 g (37%) of the title compound, melting pt. 275–277° C. (dec.).

EXAMPLE 25

2-(Cyclohexylimino)-1,2-dihydro-4-methyl-1-[3-(4-methyl-1-piperazinyl)propyl]naphtho[1,2-d]thiazol-5-ol trihydrochloride

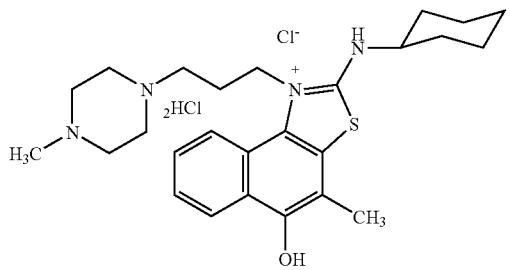

Cyclohexyl isothiocyanate (1.51 g, 10.7 mmole) in 5 mL t-butyl methyl ether was added to a solution of 1.68 g (10.7 mmole) 3-(4-methyl-1-piperazinyl)propylamine (Lancaster Synthesis, Windham N. H.) in t-butyl methyl ether (10 mL). After 18 hr at room temp., filtration gave 2.64 g (83%) 1-cyclohexyl-3-[(4-methyl-1-piperazinyl)propyl]thiourea, melting pt. 109–111° C. A solution of 2.388 g (8 mmole) of this thiourea in 12 mL ethanol containing 2.1 mL (25.2 mmole) conc. HCl was added to a warm solution of 2.755 g (16 mmole) 2-methyl-1,4-naphthoquinone in 20 mL warm ethanol with stirring. After 3 days, 1.925 g crude solid was filtered out. Of this, 1.0 g was recrystallized from 20 mL 95% methanol+80 mL acetone to give 0.927 g (40%) of the title compound, melting pt. 242–244° C.

EXAMPLE 26

2-[[3-(Dimethylamino)propyl]imino]-1,2-dihydro-1,4-dimethylnaphtho[1,2-d]-thiazol-5-ol dihydrochloride

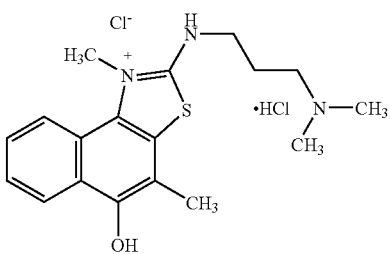

Methyl isothiocyanate (1.108 g, 15.15 mmole) in 4 mL t-butyl methyl ether was added to a solution of 1.548 g (15.15 mmole) 3-(dimethylamino)propylamine (Aldrich) in t-butyl methyl ether (10 mL). After 3 days the solution was concentrated and the residue was stored at −20° C. for 18 hr to initiate crystallization. Trituration with 1:1 t-butyl methyl ether/heptane and filtration gave 2.22 g 1-(3-dimethylamino)propyl-3-methylthiourea, melting pt. 43–45° C. A solution of this thiourea (1.753 g, 10 mmole) in ethanol (15 mL), containing 1.75 mL (21 mmole) conc. HCl, was added to a solution of 3.44 g (20 mmole) 2-methyl-1,4-naphthoquinone in 25 mL warm ethanol with stirring. After 22 hr at room temp., filtration gave 0.889 g of crude product, 0.50 g of which was recrystalized from 15 mL 95% methanol+40 mL ethyl acetate to give 0.456 g (21%) of the title compound, mp 258–260° C.

EXAMPLE 27

1,2-dihydro-1-[3-(dimethylamino)propyl]-4-methyl-2-(phenylimino)naphtho[1,2-d]thiazol-5-ol dihydrochloride

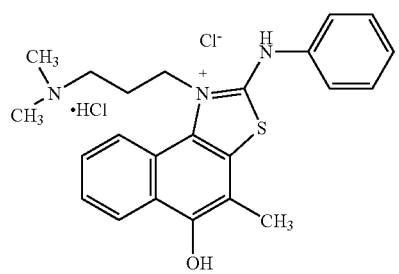

Phenyl isothiocyanate (5.283 g, 39.1 mmole) in 30 mL t-butyl methyl ether was added to a solution of 3-(dimethylamino)propylamine (3.993 g, 39.1 mmole) in 10 mL isopropanol. After stirring 2 hr at room temp., the solid which separated was filtered out and washed with t-butyl methyl ether to afford 6.51 g of 1-[3-(dimethylamino)propyl]-3-phenylthiourea (mp 112–114° C.), part of which (2.374 g, 10 mmole) was dissolved in ethanol (20 mL) containing conc. HCl (1.67 mL, 20 mmole) and added to 2-methylnaphthoquinone dissolved in warm ethanol (35 mL). After 4 days in a stoppered flask at room temp., the mixture was concentrated, and dissolved in ethyl acetate. The solid which separated after 16 hr was filtered out, but became sticky on the filter and was discarded. The filtrate was stored another 12 days at room temp. The powder which separated was filtered out to give 600 mg of pinkish-buff powder. Of this, 325 mg was recrystallized from 10 mL methanol+60 mL ethyl acetate containing a few drops of water to give 260 mg of the title compound, mp 238–240° C.

EXAMPLE 28

Methodology for Determination of Hair Stress vs. Strain Relationship (Stiffness).

The distensibility (i.e, elasticity, rigidity, shear, tensile strength, compression, etc.) of hair, nails, tendons, etc. can be easily determined using widely available commercial devices, such as manufactured by Instron. Alternatively, other test methods known to a practitioner of the art may be employed.

The test assay for determining whether hair has been "rejuvenated" for the present invention is the following. Individual scalp hairs were cemented into the ends of glass capillary tubes such that several centimeters of the shaft protruded from the end. This hair was then trimmed to extend 18 mm from the end of the tube. The unit was then inserted into a micropipette positioner for study. Evaluation consisted of bending the hair by applying a specified force and displacement. Thus, this determination of stress vs strain of bending assessed elasticity, compressibility, and shear of each hair shaft. Each hair served as its own control, with baseline and post-treatment properties assessed and directly compared.

A 1 mm thick plate with a 0.5 mm diameter hole drilled through was attached to the surface of an isometric strain gauge. To perform each measurement, the capillary tube was placed over the fenestrated plate and the hair end inserted into the hole in the plate without touching the strain gauge. The hair was then straightened, if necessary, such that its axis formed a 10 degree angle with respect to vertical. Once positioned, the hair was then lowered onto the surface of the strain gauge. The force required to bend each hair a specified distance was determined over a wide range of displacements. From the stress vs strain relationships thus derived, the work to bend each hair under different treatment regimens can be directly compared. For purposes of the present invention, the term "rejuvenated" hair shall mean an improvement of at least 20% in the measured values of the treated hair, toward the values seen in young, undamaged hair (i.e. healthy 20 year old human).

To determine changes in deformability of nails treated with a rejuvenator, a nail specimen is trimmed to standard dimensions (thickness and cross sectional area) and dried for 2 hours in an oven at 45° C. The nail is then clamped within an Instron materials testing device. A stress vs strain relationship is determined using this instrument, taking care to perform testing only within the region of reversibility (i.e., not to apply excessive stress). The nail specimen is then removed from the materials testing device and exposed to a tissue rejuvenator bath at a concentration and for a time needed to provide the desired change in deformability. The nail specimen is then washed in distilled water twice for 10 minutes each and dried in an oven at 45° C. for 2 hrs. A new stress vs strain relationship is then obtained after this treatment. This shows that the strain for a specific stress is reduced by about 50%. For purposes of the present invention, the term "rejuvenated" nail shall mean an improvement of at least 20% in the measured values of the treated nail, toward the values seen in young, undamaged nails (i.e. healthy 20 year old human).

EXAMPLE 29

Effect of Rejuvenator on Hair Deformability.

Individual hairs were prepared within capillary tubes and tested as described above. The stress versus strain relationship was determined as a baseline. Subsequently, the hair was immersed in a 10 mM solution of 1-ethyl-2-(ethylimino)-1,2-dihydro-4-methylnaphtho[1,2-d]thiazol-5-ol monohydrochloride (FP 053) for 15 minutes. The hair was then removed from the bath and rinsed for 5 minutes in distilled water and dried and re-tested. The results are shown in FIG. 1, which illustrates that after treatment with a rejuvenator, the hair possessed decreased stiffness, as indicated by the fact that for strain greater than about 0.06, the resulting stress was about 50% less than before treatment.

EXAMPLE 30

Rejuvenator Shampoo Composition.

The following shampoo composition is prepared employing a compound of the present invention and is applied to hair tresses.

| Component | Weight (%) |
|---|---|
| Sodium Lauryl Sulfate (30%) | 40.00 |
| Lauric Diethanolamide | 4.00 |

-continued

| Component | Weight (%) |
|---|---|
| 2-(Cyclohexylimino)-1,2-dihydro-4-methyl-1-[3-(dimethylamino)propyl]naphtho[1,2-d]thiazol-5-ol dihydrochloride | 1.10 |
| Perfume | 0.25 |
| Dowicil 200 | 0.20 |
| Soft Water | 54.45 |

EXAMPLE 31

Rejuvenator Nail Polish Composition.

The following nail polish composition is manufactured according to conventional methods containing the compounds of the present invention.

| Amount | Weight (%) |
|---|---|
| Nitrocellulose (¼" RS) | 15.00 |
| Nitrocellulose (½" RS) | 5.00 |
| Dipropylene Glycol Di-P-Aminobenzoate | 10.00 |
| Neopentyl Glycol Dioctanoate | 5.00 |
| Toluene | 47.80 |
| Ethyl Acetate | 10.00 |
| N-Methyl-2-Pyrrolidone | 2.00 |
| Isopropanol | 0.50 |
| 2-(Cyclohexylimino)-1,2-dihydro-4-methyl-1-[3-(dimethylamino)propyl]naphtho[1,2-d]thiazol-5-ol dihydrochloride | 2.00 |
| Stearalkonium Hectorite | 1.00 |
| Titanium Dioxide | 0.30 |
| Black Iron Oxide | 0.30 |
| D&C Red #7 Ca Lake | 0.30 |
| D&C Red #34 Ca Lake | 0.30 |
| D&C Yellow #5 Zr Lake | 0.50 |

EXAMPLE 32

Rejuvenator Nail Composition with Antifungal.

The components outlined below are mixed into a homogeneous solution which is useful for applying to finger and toe nails for rejuvenation.

| Component | Weight (%) |
|---|---|
| Alcohol SDA | 67.0 |
| Miconazole | 20.0 |
| 2-(Cyclohexylimino)-1,2-dihydro-4-methyl-1-[3-(dimethylamino)propyl]naphtho[1,2-d]thiazol-5-ol dihydrochloride | 2.0 |
| Glycerin | 1.0 |
| Water | 4.0 |
| Propylene glycol | 5.0 |
| Hydroxypropyl cellulose | 1.0 |

EXAMPLE 33

Rejuvenator Hair Conditioning Composition.

| Ingredient | Weight (%) |
| --- | --- |
| Deionized Water | 93.10 |
| Hydroxyethylcellulose | 1.35 |
| Silicone Copolymer (SF 1188 (GE)) | 0.75 |
| Oleyl Alcohol | 0.75 |
| DTAC (Lauryl Trimethyl Ammonium Chloride) | 2.25 |
| 2-(Cyclohexylimino)-1,2-dihydro-4-methyl-1-[3-(dimethyl-amino)propyl]naphtho[1,2-d]thiazol-5-ol dihydrochloride | 1.0 |
| Germaben II (preservative) | 0.50 |
| Perfume | 0.30 |

EXAMPLE 34

Tendon Rejuvenation.

Figure 2:
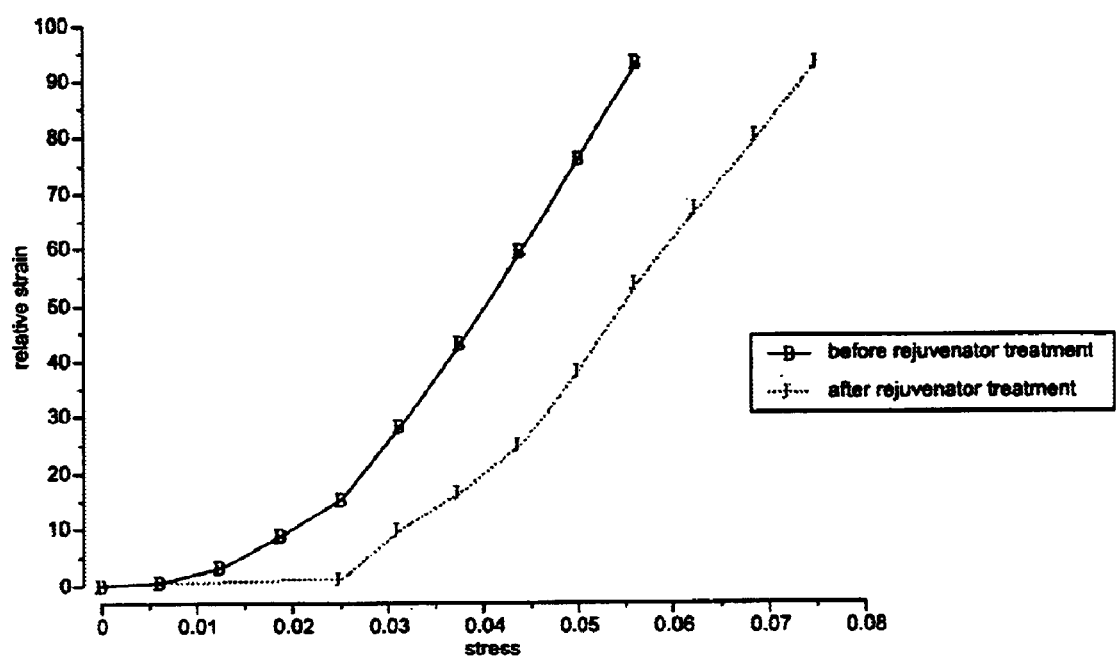
FIG. 2 shows that compositions of the present invention improve the distensibility and tensile strength of a tendon after treatment.

The elasticity of the Achilles tendon of a one year old hen was determined in a materials testing device before and after ex vivo exposure for 15 minutes to a solution containing a composition of the present invention in an amount sufficient to exert clinical effectiveness. As shown in FIG. 2, post treatment, distensibility and tensile strength was significantly improved towards that of a younger chicken.

EXAMPLE 35

Ex Vivo Rejuvenation of Lung Tissue: Diffusion Coefficient.

The following is an illustration of a methodology that can be used to rejuvenate ex vivo and prior to transplantation to a recipient patient, the lungs removed from a donor cadaver aged 21 years or more. Older subjects exhibit a decrease in the deformability of pulmonary tissue and in the capacity of gases, including oxygen, to diffuse across alveolar membranes. Individuals' deformability and diffusion characteristics can be characterized by using the standard methodology of determination of the lung diffusing capacity for carbon monoxide (e.g., Chang et al., Chest (1992) 102: 139–42). The diffusing capacity is measured in the supine patient using a single breath of carbon monoxide (0.3%) held for ten seconds using a CPI 5000 IV (Gould Instruments, Houston, Tex.), corrected for alveolar volume. A young subject (20 years old) will have approximately a 40% higher diffusion coefficient for carbon monoxide compared to older subjects (60 yrs). The ex vivo organ is flushed once with a cooled preservation solution containing a composition of the present invention at a concentration of 0.01 to 1.0 mM. Testing in the recipient patient, following transplantation of the lungs, would show that both deformability and diffusional capacity had improved to a state comparable to the one observed in the lungs of a healthy and young individual (i.e., 20 years or less).

EXAMPLE 36

Rejuvenation of Organs Composition.

A 70 year old male individual and established organ donor is declared brain dead 24 hours following a motor vehicle accident during which he sustained serious brain trauma. This individual has no known history of cardiovascular or pulmonary disease, infection with the hepatitis viruses, HIV or neoplastic processes. His organs are considered for donation. However, because of his age, donation of the kidneys, heart and lungs would generally not be indicated. The composition and method of the present invention are employed to rejuvenate the aged organs to a state compatible with the organs of a young individual, exhibiting deformability and diffusion characteristics of young organs. The regimen applied consists of the ex vivo perfusion of the extracted organs with an accepted preservation solution containing a sufficient concentration of the composition of the present invention for a sufficient duration of time, e.g., 15 minutes, following conventionally established guidelines for the preservation of cells, tissues and/or organs ex vivo. Thereafter, depending on need, the organs are continually perfused with a conventional preservation solution which may or may not contain additional concentrations of the compositions of the present invention.

The organ extraction as well as the ex vivo handling and implantation of the organ into the recipient are in accordance with established algorithms and procedures. Prior to implantation, the organ may be flushed with a conventional preservation solution. This flushing procedure permits the transplantation of an organ free of the compositions of the present invention.

It is believed that the transplanted organs, treated as described herein, would demonstrate improved functionality, both from a biomechanical and molecular diffusion/transportation perspective. Moreover, the tissue rejuvenation technology would also increase the number of transplantable organs significantly. There is a great demand for transplantable organs which is widely exceeding the available supply of transplantable organs. Alternatively, the technology would also improve the functionality of currently transplantable organs and improve survival and clinical outcome of such organs post transplantation.

EXAMPLE 37

Treatment of Age-Related Eye Diseases: Glaucoma and Presbyopia.

A. Glaucoma

Glaucoma is a leading cause of blindness. There are four major types of glaucoma:

open angle or chronic glaucoma
closed angle or acute glaucoma
congenital glaucoma
secondary glaucoma Open angle or chronic glaucoma is by far the most common type. In chronic glaucoma the outflow (Schlemm canal) of the aqueous humor is blocked. Although the precise mechanisms leading to outflow blockage have not been established, the occurrence of chronic glaucoma is associated with age above 45 years and diabetes. It is believed that decreased deformability and diffusional characteristics of the Schlemm canal and surrounding tissues are important contributing factors. The disease usually affects both eyes and, over a period of month's, the consistently elevated pressure slowly damages the optic nerve and retina.

In an embodiment of the present invention, a patient with diagnosed open angle glaucoma is treated with a medicament containing a composition of the present invention in an amount sufficient to exert clinical effectiveness. The concentration administered ranges from 0.01 to 10 mM, preferably 1 mM. The mode of administration includes, by way of non-limiting example, systemic (oral, parenteral) and topical (eye ointment, eye drops). It is believed that such treatment would induce rejuvenation of the tissues constituting the outflow system, including improved deformability and diffusional capacity, and improve outflow of aqueous humor to a state comparable to the one observed in the eyes of healthy and young individuals (i.e., 20 years or less).

B. Presbyopia

Presbyopia is an age-associated progressive loss of the focusing power of the lens, resulting in farsightedness. The focusing power of the eye, which depends upon the inherent elasticity of the lens and the ciliary body, including the ciliary muscles, is gradually lost with the aging process. This results in a gradual decrease in the ability of the eye to focus on objects that are close up. It is usually noticed around the age of 45, when one realizes the need to hold reading materials further away in order to focus on them. Presbyopia occurs in everyone to some degree during the aging process. There is no proven prevention for presbyopia.

decreased focusing ability for near objects eyestrain tired eyes headache

Diagnosis of presbyopia includes performance of a general eye examination, including an optometric examination to determine correct prescription for glasses.

In an embodiment of the present invention, a patient with a diagnosis of presbyopia is treated with a medicament containing a composition of the present invention in an amount sufficient to exert clinical effectiveness. The concentration administered ranges from 0.01 to 10 mM, preferably 1 mM. The mode of administration includes, by way of non-limiting example, systemic (oral, parenteral) and topical (eye ointment, eye drops). It is believed that such treatment would induce rejuvenation of the lens and ciliary body tissues, including improved deformability and diffusional capacity, and improve the eyes' ability to accommodate to a state comparable to the one observed in the eyes of healthy and young individuals (i.e., 20 years or less).

EXAMPLE 38

Rejuvenation of the Heart and the Vasculature.

With increasing age there is stiffening of the cardiac chambers as well as stiffening of the large and small vessels. Stiffening of the cardiac chambers may lead to diastolic dysfunction, a state of impaired relaxation of ventricles in diastole and, if advanced, to overt congestive heart failure. Diastolic dysfunction is common in individuals over 60 years of age and is associated with exercise intolerance. Stiffening of the vasculature may induce isolated systolic hypertension, a major problem in elderly people. Isolated systolic hypertension is defined as a raised systolic pressure but normal diastolic pressure (i.e., increase in pulse pressure). It affects around half of people aged over 60 years (Ramsay L E et al. *J Hum Hypertens* 1999; 13:569.92). Based on cross sectional, longitudinal, and randomised controlled trials, it is believed that isolated systolic hypertension confers a substantial cardiovascular risk (SHEP Cooperative Research Group. *JAMA* 1991;265:3255.65; Staessen J A, et al. *Lancet* 1997;350:757.64). In yet another embodiment of the present invention, a patient with diagnosed diastolic dysfunction and/or isolated systolic hypertension is treated with a medicament containing a composition of the present invention in an amount sufficient to exert clinical effectiveness. The concentration administered ranges from 0.1 to 10.0 mg/kg of body weight, preferably 1.0 mg/kg of body weight. The mode of administration includes, by way of non-limiting example, oral, rectal, transcutaneous, transpulmonary and percutaneous (e.g., intravenous, intramuscular, subcutanous) administration. It is believed that such treatment would induce rejuvenation of the cardiac and vascular tissues, including improved deformability and diffusional capacity. As a result, individuals treated with such medicament, as described herein, would demonstrate improved exercise tolerance and a decrease in systolic blood pressure (i.e., decreased pulse pressure). It is believed that such results would reduce cardiovascular morbidity and mortality of treated populations. The amount of tissue rejuvenation achieved is defined as an improvement of at least 20% in tissue deformability and diffusional capacity toward that observed in a healthy and young individual (i.e., 20 years or less).

EXAMPLE 39

Rejuvenation of the Genitourinary Tract.

The genitourinary apparatus in both male and female individuals is subject to age-related changes, contributing to the syndrome of dysuria of the elderly and encompassing signs and symptoms of urinary incontinence and obstruction (prostatism). Incontinence is defined as the inability to control urination (passage of urine). It can range from an occasional leakage of urine to a complete inability to hold any urine. In contrast, urinary obstruction is associated with a range of symptoms, including urinary hesitancy (slowed or delayed start of the urinary stream), weak urine stream, nocturia (needing to urinate 2 to 3 times per night), pain with urination, urinary retention, increased urinary frequency, strong and sudden urge to urinate (urinary urgency), and, in advanced cases, incontinence.

In view of the complex anatomical and urodynamic factors controlling urinary flow it is believed that age-related changes in the deformability and diffusional characteristics of tissues constituting the urogenital apparatus are important contributors to the clinical syndrome.

In an embodiment of the present invention, a patient with diagnosed dysuria, manifesting itself predominantly as either incontinence or obstruction, is treated with a medicament containing a composition of the present invention in an amount sufficient to exert clinical effectiveness. The concentration administered ranges from 0.1 to 10.0 mg/kg of body weight, preferably 1.0 mg/kg of body weight. The mode of administration would include, by way of non-limiting example, oral, rectal, transcutaneous, transpulmonary and percutaneous (e.g., intravenous, intramuscular, subcutanous) administration. It is believed that such treatment would induce rejuvenation of the genitourinary tissues, including improved deformability and diffusional capacity. As a result, individuals treated with such medicament, as described herein, would demonstrate improved urination (i.e., decreased hesitency or urge). It is expected that such results would reduce signs and symptoms, as listed herein, of treated populations. The amount of tissue rejuvenation achieved is defined as an improvement of at least 20% in tissue deformability and diffusional capacity toward that observed in a healthy and young individual (i.e., 20 years or less).

EXAMPLE 40

Rejuvenation of Aged Skin.

The integument undergoes visible changes as a function of aging and exposure to environmental influences, predominantly UV radiation contained in sun light. Age-related changes include loss of elasticity, thinning, reduction in water content and an increased incidence of mitotic activity (i.e., benign skin lesions, such as actinic keratosis and malignant tumors, such as squamous cell cancer). The physical changes occurring in aged skin are typically described as wrinkling and sagging of the skin.

In a further embodiment of the present invention, a patient with a diagnosis of aged skin is treated with a medicament containing a composition of the present invention in an amount sufficient to exert clinical effectiveness. The concentration administered ranges from 0.01 to 10 mM, preferably 1 mM. The mode of administration would include, by way of non-limiting example, topical (e.g., ointment, creme, solution, with or without occlusive dressing) and intracutanous administration (by needle or jet stream). It is believed that such treatment would induce rejuvenation of the integument, including improved skin elasticity and turgor, resulting in decreased wrinkling and sagging. The amount of tissue rejuvenation achieved is defined as an improvement of at least 20% in tissue elasticity and turgor toward a state observed in a healthy and young individual (i.e., 20 years or less).

EXAMPLE 41

Rejuvenation of Lung Tissue in Patients with Chronic Obstructive Pulmonary disease.

Older subjects exhibit a decrease in the deformability of pulmonary tissue and in the capacity of gases, including oxygen, to diffuse across alveolar membranes. These age-related changes in pulmonary function are exacerbated in smokers and subjects exposed to certain environmental agents, leading to pneumoconiosis secondary to the exposure to silica, kaolin, mica, beryllium, copper, basalt, cobalt, and other minerals. Lung tissue deformability is determined through pulmonary function testing, comprising the measurement of lung volume in inspiration and expiration, and determination of flow characteristics. Diffusion characteristics can be evaluated by using the standard methodology of determination of the lung diffusing capacity for carbon monoxide (e.g., Chang et al., Chest (1992) 102:139–42). The diffusing capacity is measured in the supine patient using a single breath of carbon monoxide (0.3%) held for ten seconds using a CPI 5000 IV (Gould Instruments, Houston, Tex.), corrected for alveolar volume. A young subject (20 years old) will have approximately a 40% higher diffusion coefficient for carbon monoxide compared to older subjects (60 years old).

The following is a further embodiment of the present invention that is used to rejuvenate the lungs of an aged male patient with chronic obstructive pulmonary disease due to a 50 pack year smoking history. The patient is complaining of shortness of breath at minimal exercise levels and chronic productive cough. The patient is treated with a medicament containing a composition of the present invention in an amount sufficient to exert clinical effectiveness. The concentration administered would range from 0.1 to 10.0 mg/kg of body weight, preferably 1.0 mg/kg of body weight. The mode of administration includes, by way of non-limiting example, oral, rectal, transcutaneous, transpulmonary and percutaneous (e.g., intravenous, intramuscular, subcutanous) administration. It is believed that such treatment would induce rejuvenation of the pulmonary tissues, resulting in improved deformability and diffusional capacity. As a result, individuals treated with such medicament, as described herein, would demonstrate improved exercise tolerance. The amount of tissue rejuvenation achieved is defined as an improvement of at least 20% in tissue deformability and diffusional capacity toward that observed in a healthy and young individual (i.e., 20 years or less).

EXAMPLE 42

Barrier to Diffusion

Changes in the diffusion barrier characteristics of tissues can have significant adverse consequences on biological processes. One specific area for which these effects are especially troublesome is that of complex feedback or feedforward systems. In these, changes in the characteristics of the barrier to diffusion of substances that the concentration of substances which are actively regulated produce a hysteresis in the entire control system.

As an example, a patient with diabetes mellitus poorly controlled over 10 years has significantly increased cross-linking of tissues, including the vasculature of the adrenal cortex. Adrenocorticotrophic hormone secreted from the anterior pituitary reaches the adrenal cortical cells producing cortisol with a significant delay caused by the increased resistance to diffusion of ACTH across capillaries of the adrenal gland. Because of this delay, inappropriately prolonged secretion of ACTH is maintained, until sufficient cortisol is produced to shut off ACTH. Therefore, sequential temporal measurements of the diurnal secretory pattern in this diabetic individual shows an abnormal cortisol secretion profile characterized by an increase in total cortisol secreted, as well as a delay to peak concentration in the serum. Further, the peak ACTH levels are increased compared to normal. Treatment with a medicament containing a composition of the present invention, in an amount sufficient to exert clinical effectiveness, uncouples the proteins which are responsible for the diffusional delay of ACTH reaching the adrenal cortical cells. Subsequent plasma sequential sampling shows that the previously abnormal patterns of ACTH and cortisol secretion have been normalized by treatment.

What is claimed is:

1. A composition for the treatment of hair, nail, ex-vivo organ, ex-vivo cell or ex-vivo tissue to improve the biomechanical and diffusional characteristics comprising an effective amount of a compound selected form the group consisting of compounds of the formula (I):

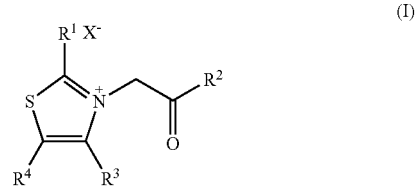

wherein

R' is a $C_1$–$C_{18}$ alkyl group —CH($R^5$)—OH, or the group —CH($R^5$)—OC(=O)—$R^6$ wherein $R_5$ is a $C_{1\text{-}18}$ alkyl group and $R_6$ is selected from the group consisting of $C_1$–$C_{18}$ alkyl, phenyl, halosubstituted phenyl, $C_1$–$C_{18}$ alkoxysubstituted phenyl and naphthyl; $R_2$ is selected from the group consisting of hydroxy, phenyl, halosubstituted phenyl, $C_1$–$C_{18}$ alkoxysubstituted phenyl, a $C_{5\text{-}7}$ aromatic, unsaturated or saturated heterocyclic ring having one to three heteroatoms selected from the group consisting of N, O and S; $R_3$ and $R_4$ together with their ring atoms may be an aromatic ring system of 6–10 carbons, optionally substituted with one or more halo, lower alkyl, lower alkoxy, or amino groups; and $X^-$ is halide or other pharmaceutically acceptable anion.

* * * * *